(12) United States Patent
Salahieh et al.

(10) Patent No.: US 7,824,443 B2
(45) Date of Patent: Nov. 2, 2010

(54) MEDICAL IMPLANT DELIVERY AND DEPLOYMENT TOOL

(75) Inventors: Amr Salahieh, Saratoga, CA (US);
Dwight Morejohn, Davis, CA (US);
Ulrich R. Haug, Campbell, CA (US);
Brian Brandt, San Jose, CA (US); Hans Valencia, San Jose, CA (US); Tom Saul, Moss Beach, CA (US)

(73) Assignee: Sadra Medical, Inc., Los Gatos, CA (US)

( * ) Notice: Subject to any disclaimer, the term of this patent is extended or adjusted under 35 U.S.C. 154(b) by 1177 days.

(21) Appl. No.: 11/275,912

(22) Filed: Feb. 2, 2006

(65) Prior Publication Data
US 2006/0173524 A1    Aug. 3, 2006

Related U.S. Application Data

(63) Continuation-in-part of application No. 10/982,388, filed on Nov. 5, 2004, which is a continuation-in-part of application No. 10/746,120, filed on Dec. 23, 2003, now abandoned, and a continuation-in-part of application No. 10/870,340, filed on Jun. 16, 2004.

(51) Int. Cl.
*A61F 2/24* (2006.01)

(52) U.S. Cl. ..................................... 623/2.11

(58) Field of Classification Search ................ 623/1.24, 623/1.26, 2.14, 2.18, 2.11; 606/106, 108, 606/191–195
See application file for complete search history.

(56) References Cited

U.S. PATENT DOCUMENTS 3,334,629 A    8/1967    Cohn
3,409,013 A    11/1968   Berry
3,540,431 A    11/1970   Mobin-Uddin (Continued)

FOREIGN PATENT DOCUMENTS

CN    1338951 A    3/2002

(Continued)

OTHER PUBLICATIONS

Salahieh, et al., U.S. Appl. No. 12/264,082 entitled "Repositionable heart valve and method," filed Nov. 3, 2008.

(Continued)

*Primary Examiner*—Alvin J Stewart
(74) *Attorney, Agent, or Firm*—Shay Glenn LLP

(57) ABSTRACT

An apparatus for endovascularly replacing a patient's heart valve. In some embodiments, the apparatus includes a replacement heart valve implant comprising a valve and an expandable anchor; and a deployment tool adapted to endovascularly deliver the replacement heart valve implant to an implant site within the patient, the deployment tool comprising an actuator adapted to exert an axially directed force on the anchor. The invention also provides a method for endovascularly replacing a heart valve of a patient. In some embodiments, the method includes the steps of endovascularly delivering a replacement heart valve implant having a valve and an anchor to an implant site within the patient; and applying an axially directed force from an actuator outside of the patient to the anchor. In invention also provides deployment tools for performing the method.

39 Claims, 19 Drawing Sheets

U.S. PATENT DOCUMENTS

| | | | |
|---|---|---|---|
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,580,568 A | 4/1986 | Gianturco |
| 4,602,911 A | 7/1986 | Ahmadi et al. |
| 4,610,688 A | 9/1986 | Silvestrini et al. |
| 4,617,932 A | 10/1986 | Kornberg |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Igoe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,909,252 A | 3/1990 | Goldberger |
| 4,917,102 A | 4/1990 | Miller et al. |
| 4,954,126 A | 9/1990 | Wallsten |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,217,483 A | 6/1993 | Tower |
| 5,258,042 A | 11/1993 | Mehta |
| 5,332,402 A | 7/1994 | Teitelbaum |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A | 8/1995 | Schmitt |
| 5,476,506 A | 12/1995 | Lunn |
| 5,476,510 A * | 12/1995 | Eberhardt et al. .......... 623/2.11 |
| 5,480,423 A | 1/1996 | Ravenscroft et al. |
| 5,507,767 A | 4/1996 | Maeda et al. |
| 5,545,133 A | 8/1996 | Burns et al. |
| 5,545,211 A | 8/1996 | An et al. |
| 5,549,665 A | 8/1996 | Vesely et al. |
| 5,554,185 A | 9/1996 | Block et al. |
| 5,573,520 A | 11/1996 | Schwartz et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,713,953 A | 2/1998 | Vallana et al. |
| 5,716,370 A | 2/1998 | Williamson, IV et al. |
| 5,720,391 A | 2/1998 | Dohm et al. |
| 5,733,325 A | 3/1998 | Robinson et al. |
| 5,735,842 A | 4/1998 | Krueger et al. |
| 5,769,812 A | 6/1998 | Stevens et al. |
| 5,800,456 A | 9/1998 | Maeda et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A * | 11/1999 | Robertson et al. .......... 623/2.11 |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,123,723 A | 9/2000 | Konya et al. |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,179,859 B1 | 1/2001 | Bates |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,258,114 B1 | 7/2001 | Konya et al. |
| 6,258,115 B1 | 7/2001 | Dubrul |
| 6,258,120 B1 | 7/2001 | McKenzie et al. |
| 6,267,783 B1 | 7/2001 | Letendre et al. |

| | | | | | | |
|---|---|---|---|---|---|---|
| 6,270,513 B1 | 8/2001 | Tsugita et al. | 6,773,454 B2 | 8/2004 | Wholey et al. | |
| 6,277,555 B1 | 8/2001 | Duran et al. | 6,776,791 B1 | 8/2004 | Stallings et al. | |
| 6,309,417 B1 | 10/2001 | Spence et al. | 6,790,229 B1 * | 9/2004 | Berreklouw ................. | 623/2.1 |
| 6,319,281 B1 | 11/2001 | Patel | 6,790,230 B2 | 9/2004 | Beyersdorf et al. | |
| 6,327,772 B1 | 12/2001 | Zadno-Azizi et al. | 6,790,237 B2 | 9/2004 | Stinson | |
| 6,336,934 B1 | 1/2002 | Gilson et al. | 6,792,979 B2 | 9/2004 | Konya et al. | |
| 6,336,937 B1 | 1/2002 | Vonesh et al. | 6,814,746 B2 | 11/2004 | Thompson et al. | |
| 6,338,735 B1 | 1/2002 | Stevens | 6,821,297 B2 | 11/2004 | Snyders | |
| 6,348,063 B1 | 2/2002 | Yassour et al. | 6,837,901 B2 | 1/2005 | Rabkin et al. | |
| 6,352,708 B1 | 3/2002 | Duran et al. | 6,840,957 B2 | 1/2005 | DiMatteo et al. | |
| 6,361,545 B1 | 3/2002 | Macoviak et al. | 6,843,802 B1 | 1/2005 | Villalobos et al. | |
| 6,371,970 B1 | 4/2002 | Khosravi et al. | 6,849,085 B2 | 2/2005 | Marton | |
| 6,371,983 B1 | 4/2002 | Lane | 6,863,668 B2 | 3/2005 | Gillespie et al. | |
| 6,379,383 B1 | 4/2002 | Palmaz et al. | 6,872,223 B2 | 3/2005 | Roberts et al. | |
| 6,398,807 B1 | 6/2002 | Chouinard et al. | 6,872,226 B2 | 3/2005 | Cali et al. | |
| 6,409,750 B1 | 6/2002 | Hyodoh et al. | 6,875,231 B2 | 4/2005 | Anduiza et al. | |
| 6,416,510 B1 | 7/2002 | Altman et al. | 6,881,220 B2 | 4/2005 | Edwin et al. | |
| 6,425,916 B1 | 7/2002 | Garrison et al. | 6,887,266 B2 | 5/2005 | Williams et al. | |
| 6,440,164 B1 | 8/2002 | DiMatteo et al. | 6,890,340 B2 | 5/2005 | Duane | |
| 6,454,799 B1 | 9/2002 | Schreck | 6,893,459 B1 * | 5/2005 | Macoviak ................... | 623/2.11 |
| 6,458,153 B1 | 10/2002 | Bailey et al. | 6,893,460 B2 | 5/2005 | Spenser et al. | |
| 6,468,303 B1 | 10/2002 | Amplatz et al. | 6,905,743 B1 | 6/2005 | Chen et al. | |
| 6,475,239 B1 | 11/2002 | Campbell et al. | 6,908,481 B2 | 6/2005 | Cribier | |
| 6,482,228 B1 | 11/2002 | Norred | 6,911,036 B2 | 6/2005 | Douk et al. | |
| 6,485,502 B2 | 11/2002 | Don Michael et al. | 6,911,043 B2 | 6/2005 | Myers et al. | |
| 6,494,909 B2 | 12/2002 | Greenhalgh | 6,936,058 B2 | 8/2005 | Forde et al. | |
| 6,503,272 B2 | 1/2003 | Duerig et al. | 6,936,067 B2 | 8/2005 | Buchanan | |
| 6,508,833 B2 | 1/2003 | Pavcnik et al. | 6,953,332 B1 | 10/2005 | Kurk et al. | |
| 6,527,800 B1 | 3/2003 | McGuckin, Jr. et al. | 6,964,673 B2 | 11/2005 | Tsugita et al. | |
| 6,530,949 B2 | 3/2003 | Konya et al. | 6,969,395 B2 | 11/2005 | Eskuri | |
| 6,537,297 B2 | 3/2003 | Tsugita et al. | 6,974,464 B2 | 12/2005 | Quijano et al. | |
| 6,540,768 B1 | 4/2003 | Diaz et al. | 6,974,474 B2 | 12/2005 | Pavcnik et al. | |
| 6,562,058 B2 | 5/2003 | Seguin et al. | 6,974,476 B2 | 12/2005 | McGuckin, Jr. et al. | |
| 6,592,546 B1 | 7/2003 | Barbut et al. | 6,979,350 B2 | 12/2005 | Moll et al. | |
| 6,592,614 B2 | 7/2003 | Lenker et al. | 6,984,242 B2 | 1/2006 | Campbell et al. | |
| 6,610,077 B1 | 8/2003 | Hancock et al. | 7,011,681 B2 * | 3/2006 | Vesely ...................... | 623/2.11 |
| 6,616,682 B2 | 9/2003 | Joergensen et al. | 7,018,406 B2 | 3/2006 | Seguin et al. | |
| 6,622,604 B1 | 9/2003 | Chouinard et al. | 7,025,791 B2 | 4/2006 | Levine et al. | |
| 6,623,518 B2 | 9/2003 | Thompson et al. | 7,037,331 B2 | 5/2006 | Mitelberg et al. | |
| 6,632,243 B1 | 10/2003 | Zadno-Azizi et al. | 7,041,132 B2 * | 5/2006 | Quijano et al. ............. | 623/2.11 |
| 6,635,068 B1 | 10/2003 | Dubrul et al. | 7,122,020 B2 | 10/2006 | Mogul | |
| 6,635,079 B2 | 10/2003 | Unsworth et al. | 7,166,097 B2 | 1/2007 | Barbut | |
| 6,652,571 B1 | 11/2003 | White et al. | 7,175,653 B2 | 2/2007 | Gaber | |
| 6,652,578 B2 | 11/2003 | Bailey et al. | 7,175,654 B2 | 2/2007 | Bonsignore et al. | |
| 6,663,588 B2 | 12/2003 | DuBois et al. | 7,189,258 B2 | 3/2007 | Johnson et al. | |
| 6,663,663 B2 | 12/2003 | Kim et al. | 7,191,018 B2 | 3/2007 | Gielen et al. | |
| 6,669,724 B2 | 12/2003 | Park et al. | 7,235,093 B2 | 6/2007 | Gregorich | |
| 6,673,089 B1 | 1/2004 | Yassour et al. | 7,258,696 B2 | 8/2007 | Rabkin et al. | |
| 6,673,109 B2 | 1/2004 | Cox | 7,374,560 B2 | 5/2008 | Ressemann et al. | |
| 6,676,692 B2 | 1/2004 | Rabkin et al. | 7,632,298 B2 | 12/2009 | Hijlkema et al. | |
| 6,676,698 B2 | 1/2004 | McGuckin, Jr. et al. | 2001/0039450 A1 | 11/2001 | Pavcnik et al. | |
| 6,682,543 B2 | 1/2004 | Barbut et al. | 2001/0041928 A1 | 11/2001 | Pavcnik et al. | |
| 6,682,558 B2 | 1/2004 | Tu et al. | 2001/0041930 A1 | 11/2001 | Globerman et al. | |
| 6,682,559 B2 | 1/2004 | Myers et al. | 2001/0044634 A1 | 11/2001 | Don Michael et al. | |
| 6,685,739 B2 | 2/2004 | DiMatteo et al. | 2001/0044652 A1 | 11/2001 | Moore | |
| 6,689,144 B2 | 2/2004 | Gerberding | 2001/0044656 A1 * | 11/2001 | Williamson et al. ........ | 623/2.11 |
| 6,689,164 B1 | 2/2004 | Seguin | 2002/0002396 A1 | 1/2002 | Fulkerson | |
| 6,692,512 B2 | 2/2004 | Jang | 2002/0010489 A1 | 1/2002 | Grayzel et al. | |
| 6,695,864 B2 | 2/2004 | Macoviak et al. | 2002/0029981 A1 | 3/2002 | Nigam | |
| 6,695,865 B2 | 2/2004 | Boyle et al. | 2002/0032481 A1 | 3/2002 | Gabbay | |
| 6,702,851 B1 | 3/2004 | Chinn et al. | 2002/0055769 A1 | 5/2002 | Wang | |
| 6,712,842 B1 | 3/2004 | Gifford et al. | 2002/0058995 A1 | 5/2002 | Stevens | |
| 6,712,843 B2 | 3/2004 | Elliott | 2002/0077696 A1 | 6/2002 | Zadno-Azizi et al. | |
| 6,714,842 B1 | 3/2004 | Ito | 2002/0082609 A1 | 6/2002 | Green | |
| 6,719,789 B2 | 4/2004 | Cox | 2002/0095173 A1 | 7/2002 | Mazzocchi et al. | |
| 6,730,118 B2 | 5/2004 | Spenser et al. | 2002/0095209 A1 | 7/2002 | Zadno-Azizi et al. | |
| 6,730,377 B2 | 5/2004 | Wang | 2002/0111674 A1 | 8/2002 | Chouinard et al. | |
| 6,733,525 B2 | 5/2004 | Pease et al. | 2002/0120328 A1 | 8/2002 | Pathak et al. | |
| 6,736,846 B2 | 5/2004 | Cox | 2002/0151970 A1 | 10/2002 | Garrison et al. | |
| 6,752,828 B2 | 6/2004 | Thornton | 2002/0161392 A1 | 10/2002 | Dubrul | |
| 6,758,855 B2 | 7/2004 | Fulton, III et al. | 2002/0161394 A1 | 10/2002 | Macoviak et al. | |
| 6,764,509 B2 | 7/2004 | Chinn et al. | 2002/0177766 A1 | 11/2002 | Mogul | |
| 6,767,345 B2 | 7/2004 | St. Germain et al. | 2002/0183781 A1 | 12/2002 | Casey et al. | |

| | | | | | | |
|---|---|---|---|---|---|---|
| 2002/0188341 A1* | 12/2002 | Elliott .................. 623/1.1 | 2005/0096736 A1 | 5/2005 | Osse et al. | |
| 2002/0188344 A1 | 12/2002 | Bolea et al. | 2005/0096738 A1 | 5/2005 | Cali et al. | |
| 2003/0023303 A1 | 1/2003 | Palmaz et al. | 2005/0100580 A1 | 5/2005 | Osborne et al. | |
| 2003/0036791 A1 | 2/2003 | Philipp et al. | 2005/0107822 A1 | 5/2005 | WasDyke | |
| 2003/0040771 A1 | 2/2003 | Hyodoh et al. | 2005/0113910 A1 | 5/2005 | Paniagua et al. | |
| 2003/0040772 A1 | 2/2003 | Hyodoh et al. | 2005/0137686 A1 | 6/2005 | Salahieh et al. | |
| 2003/0050694 A1* | 3/2003 | Yang et al. ............. 623/2.11 | 2005/0137687 A1 | 6/2005 | Salahieh et al. | |
| 2003/0055495 A1 | 3/2003 | Pease et al. | 2005/0137688 A1 | 6/2005 | Salahieh et al. | |
| 2003/0060844 A1 | 3/2003 | Borillo et al. | 2005/0137689 A1 | 6/2005 | Salahieh et al. | |
| 2003/0070944 A1 | 4/2003 | Nigam | 2005/0137690 A1 | 6/2005 | Salahieh et al. | |
| 2003/0109924 A1 | 6/2003 | Cribier | 2005/0137691 A1 | 6/2005 | Salahieh et al. | |
| 2003/0109930 A1 | 6/2003 | Bluni et al. | 2005/0137692 A1 | 6/2005 | Haug et al. | |
| 2003/0125795 A1 | 7/2003 | Pavcnik et al. | 2005/0137693 A1 | 6/2005 | Haug et al. | |
| 2003/0130729 A1 | 7/2003 | Paniagua et al. | 2005/0137694 A1 | 6/2005 | Haug et al. | |
| 2003/0144732 A1 | 7/2003 | Cosgrove et al. | 2005/0137695 A1 | 6/2005 | Salahieh et al. | |
| 2003/0149476 A1 | 8/2003 | Damm et al. | 2005/0137696 A1 | 6/2005 | Salahieh et al. | |
| 2003/0149478 A1 | 8/2003 | Figulla et al. | 2005/0137697 A1 | 6/2005 | Salahieh et al. | |
| 2003/0176884 A1 | 9/2003 | Berrada et al. | 2005/0137698 A1 | 6/2005 | Salahieh et al. | |
| 2003/0181850 A1 | 9/2003 | Diamond et al. | 2005/0137699 A1 | 6/2005 | Salahieh et al. | |
| 2003/0187495 A1 | 10/2003 | Cully et al. | 2005/0137701 A1 | 6/2005 | Salahieh et al. | |
| 2003/0199913 A1 | 10/2003 | Dubrul et al. | 2005/0137702 A1 | 6/2005 | Haug et al. | |
| 2003/0199971 A1 | 10/2003 | Tower et al. | 2005/0143809 A1 | 6/2005 | Salahieh et al. | |
| 2003/0199972 A1 | 10/2003 | Zadno-Azizi et al. | 2005/0165352 A1 | 7/2005 | Henry et al. | |
| 2003/0208224 A1 | 11/2003 | Broome | 2005/0165477 A1 | 7/2005 | Anduiza et al. | |
| 2003/0212429 A1 | 11/2003 | Keegan et al. | 2005/0182486 A1 | 8/2005 | Gabbay | |
| 2003/0212452 A1 | 11/2003 | Zadno-Azizi et al. | 2005/0197694 A1 | 9/2005 | Pai et al. | |
| 2003/0212454 A1 | 11/2003 | Scott et al. | 2005/0197695 A1 | 9/2005 | Stacchino et al. | |
| 2003/0216774 A1 | 11/2003 | Larson | 2005/0203614 A1 | 9/2005 | Forster | |
| 2003/0229390 A1 | 12/2003 | Ashton et al. | 2005/0203615 A1 | 9/2005 | Forster | |
| 2003/0233117 A1 | 12/2003 | Adams et al. | 2005/0203616 A1 | 9/2005 | Cribier | |
| 2004/0034411 A1 | 2/2004 | Quijano et al. | 2005/0203617 A1 | 9/2005 | Forster et al. | |
| 2004/0039436 A1 | 2/2004 | Spenser et al. | 2005/0209580 A1 | 9/2005 | Freyman | |
| 2004/0049224 A1 | 3/2004 | Buehlmann et al. | 2005/0228472 A1 | 10/2005 | Case et al. | |
| 2004/0049226 A1 | 3/2004 | Keegan et al. | 2005/0251250 A1 | 11/2005 | Verhoeven et al. | |
| 2004/0049262 A1 | 3/2004 | Obermiller et al. | 2005/0251251 A1 | 11/2005 | Cribier | |
| 2004/0073198 A1 | 4/2004 | Gilson et al. | 2005/0261759 A1 | 11/2005 | Lambrecht et al. | |
| 2004/0082904 A1 | 4/2004 | Houde et al. | 2005/0267560 A1 | 12/2005 | Bates | |
| 2004/0082967 A1 | 4/2004 | Broome et al. | 2005/0283231 A1 | 12/2005 | Haug et al. | |
| 2004/0088045 A1 | 5/2004 | Cox | 2005/0283962 A1 | 12/2005 | Boudjemline | |
| 2004/0093016 A1 | 5/2004 | Root et al. | 2006/0004439 A1 | 1/2006 | Spenser et al. | |
| 2004/0098022 A1 | 5/2004 | Barone | 2006/0004442 A1 | 1/2006 | Spenser et al. | |
| 2004/0098098 A1* | 5/2004 | McGuckin et al. ......... 623/1.14 | 2006/0015168 A1 | 1/2006 | Gunderson | |
| 2004/0098099 A1 | 5/2004 | McCullagh et al. | 2006/0155312 A1 | 7/2006 | Levine et al. | |
| 2004/0111096 A1 | 6/2004 | Tu et al. | 2006/0161249 A1 | 7/2006 | Realyvasquez et al. | |
| 2004/0116951 A1 | 6/2004 | Rosengart | 2006/0195183 A1* | 8/2006 | Navia et al. ............. 623/2.18 |
| 2004/0117004 A1 | 6/2004 | Osborne et al. | 2006/0259134 A1* | 11/2006 | Schwammenthal et al. | 623/2.11 |
| 2004/0122468 A1 | 6/2004 | Yodfat et al. | 2006/0271166 A1 | 11/2006 | Thill et al. | |
| 2004/0127936 A1 | 7/2004 | Salahieh et al. | 2007/0016286 A1 | 1/2007 | Herrmann et al. | |
| 2004/0127979 A1 | 7/2004 | Wilson et al. | 2008/0269878 A1* | 10/2008 | Iobbi .................. 623/2.11 |
| 2004/0133274 A1 | 7/2004 | Webler et al. | 2008/0288054 A1 | 11/2008 | Pulnev et al. | |
| 2004/0138694 A1 | 7/2004 | Tran et al. | 2009/0222076 A1 | 9/2009 | Figulla et al. | |
| 2004/0138742 A1 | 7/2004 | Myers et al. | | | | |
| 2004/0153094 A1 | 8/2004 | Dunfee et al. | | | | |
| 2004/0158277 A1 | 8/2004 | Lowe et al. | FOREIGN PATENT DOCUMENTS | | | |
| 2004/0167565 A1 | 8/2004 | Beulke et al. | EP | 0409929 B1 | 4/1997 | |
| 2004/0181140 A1 | 9/2004 | Falwell et al. | EP | 1000590 A1 | 5/2000 | |
| 2004/0186563 A1 | 9/2004 | Lobbi | EP | 1057459 A1 | 12/2000 | |
| 2004/0204755 A1 | 10/2004 | Robin | EP | 1057460 A1 | 12/2000 | |
| 2004/0215331 A1 | 10/2004 | Chew et al. | EP | 0937439 B1 | 9/2003 | |
| 2004/0215339 A1 | 10/2004 | Drasler et al. | EP | 1340473 A2 | 9/2003 | |
| 2004/0225321 A1 | 11/2004 | Krolik et al. | EP | 1356793 A2 | 10/2003 | |
| 2004/0254636 A1 | 12/2004 | Flagle et al. | EP | 1042045 B1 | 5/2004 | |
| 2005/0033402 A1 | 2/2005 | Cully et al. | EP | 0819013 B1 | 6/2004 | |
| 2005/0043711 A1 | 2/2005 | Corcoran et al. | EP | 1229864 B1 | 4/2005 | |
| 2005/0075662 A1 | 4/2005 | Pedersen et al. | EP | 1430853 A2 | 6/2005 | |
| 2005/0085841 A1 | 4/2005 | Eversull et al. | EP | 1059894 B1 | 7/2005 | |
| 2005/0085842 A1 | 4/2005 | Eversull et al. | EP | 1078610 B1 | 8/2005 | |
| 2005/0085843 A1 | 4/2005 | Opolski et al. | EP | 1576937 A2 | 9/2005 | |
| 2005/0085890 A1 | 4/2005 | Rasmussen et al. | EP | 1582178 A2 | 10/2005 | |
| 2005/0090846 A1 | 4/2005 | Pedersen et al. | EP | 1582179 A2 | 10/2005 | |
| 2005/0096692 A1 | 5/2005 | Linder et al. | EP | 1469797 B1 | 11/2005 | |
| 2005/0096734 A1 | 5/2005 | Majercak et al. | EP | 1600121 A1 | 11/2005 | |
| 2005/0096735 A1 | 5/2005 | Hojeibane et al. | EP | 1156757 B1 | 12/2005 | |

| | | |
|---|---|---|
| EP | 1616531 A2 | 1/2006 |
| WO | WO 93/15693 A1 | 8/1993 |
| WO | WO 95/04556 A2 | 2/1995 |
| WO | WO 95/29640 A1 | 11/1995 |
| WO | WO 96/14032 A1 | 5/1996 |
| WO | WO 96/24306 A1 | 8/1996 |
| WO | WO 98/36790 A1 | 8/1998 |
| WO | WO 98/50103 A1 | 11/1998 |
| WO | WO 98/57599 A2 | 12/1998 |
| WO | WO 99/44542 A2 | 9/1999 |
| WO | WO 00/09059 A2 | 2/2000 |
| WO | WO 00/44308 A2 | 8/2000 |
| WO | WO 00/44313 A1 | 8/2000 |
| WO | WO 00/49970 A1 | 8/2000 |
| WO | WO 00/67661 A2 | 11/2000 |
| WO | WO 01/05331 A1 | 1/2001 |
| WO | WO 01/08596 A1 | 2/2001 |
| WO | WO 01/10320 A1 | 2/2001 |
| WO | WO 01/10343 A1 | 2/2001 |
| WO | WO 01/35870 A1 | 5/2001 |
| WO | WO 01/64137 A1 | 9/2001 |
| WO | WO 02/36048 A1 | 5/2002 |
| WO | WO 02/41789 A2 | 5/2002 |
| WO | WO 02/100297 A2 | 12/2002 |
| WO | WO 03/003943 A2 | 1/2003 |
| WO | WO 03/003949 A2 | 1/2003 |
| WO | WO 03/011195 A2 | 2/2003 |
| WO | WO 03/015851 A1 | 11/2003 |
| WO | WO 2004/014256 A1 | 2/2004 |
| WO | WO 2004/019811 A2 | 3/2004 |
| WO | WO 2004/023980 A2 | 3/2004 |
| WO | WO 2004/026117 A2 | 4/2004 |
| WO | WO 2004/041126 A1 | 5/2004 |
| WO | WO 2004/047681 A1 | 6/2004 |
| WO | WO 2004/066876 A1 | 8/2004 |
| WO | WO 2004/082536 A1 | 9/2004 |
| WO | WO 2005/084595 A1 | 9/2005 |
| WO | WO 2005/087140 A1 | 9/2005 |

OTHER PUBLICATIONS

Salahieh, et al., U.S. Appl. No. 12/269,213 entitled "Everting heart valve," filed Nov. 12, 2008.
Salahieh, et al., U.S. Appl. No. 11/531,980, "Externally expandable heart valve anchor and method," filed Sep. 14, 2006.
Salahieh, et al., U.S. Appl. No. 11/532,019, "Methods and apparatus for endovascularly replacing heart valve," filed Sep. 14, 2006.
Haug, et al; U.S. Appl. No. 11/716,123, entitled "Methods and apparatus for endovascularly replacing a heart valve," filed Mar. 9, 2007.
Salahieh, et al; U.S. Appl. No. 11/706,549, entitled "Systems and Methods for Delivering a Medical Implant," filed Feb. 14, 2007.
Salahieh, et al; U.S. Appl. No. 11/732,906 entitled "Assessing the location and performance of replacement heart valves," filed Apr. 4, 2007.
Haug et al.; U.S. Appl. No. 12/028,452 entitled "Methods and apparatus for endovascularly replacing a patient's heart valve," filed Feb. 8, 2008.
Andersen, H.R. et al. "Transluminal implantation of artificial heart valves. Description of a new expandable aortic valve and initial results with implantation by catheter technique in closed chest pigs." *Euro. Heart J.* 1992; 13:704-708.
Atwood, A. et al. "Insertion of Heart Valves by Catheterization." Project Supervised by Prof. S. Muftu of Northeaster University 2001-2002: 36-40.
Bodnar, E. et al. Replacement Cardiac Valves—Chapter 13: Extinct cardiac valve prostheses. *Pergamon Publishing Corporation.* New York, 1991: 307-322.
Boudjemline, Y. et al. "Percutaneious implantation of a biological valve in the aorta to treat aortic valve insufficiency—a sheep study." *Med Sci. Monit.* 2002; vol. 8, No. 4: BR113-116.
Boudjemline, Y. et al. "Percutaneous implantation of a valve in the descending aorta in lambs." *Euro. Heart J.* 2002; 23: 1045-1049.

Boudjemline, Y. et al. "Percutaneous pulmonary valve replacement in a large right ventricular outflow tract: an experimental study." *Journal of the Americal College of Cardiology.* 2004; vol. 43(6): 1082-1087.
Boudjemline, Y. et al. "Percutaneous valve insertion: A new approach?" *J. of Thoracic and Cardio. Surg.* 2003; 125(3): 741-743.
Boudjemline, Y. et al. "Steps Toward Percutaneous Aortic Valve Replacement." *Circulation.* 2002; 105: 775-778.
Cribier, A. et al. "Early Experience with Percutaneous Transcatheter Implantation of Heart Valve Prosthesis for the Treatment of End-Stage Inoperable Patients with Calcific Aortic Stenosis." *J. of Am. Coll. of Cardio.* 2004; 43(4): 698-703.
Cribier, A., et al. "Percutaneous Transcatheter Implantation of an Aortic Valve Prosthesis for Calcific Aortic Stenosis: First Human Case Description." *Circulation.* 2002; 106: 3006-3008.
Cribier, A., et al. "Percutaneous Transcatheter Implantation of an Aortic Valve Prosthesis for Calcific Aortic Stenosis: First Human Case." *Percutaneous Valve Technologies, Inc.* 2002: 16 pages.
Ferrari, M. et al. "Percutaneous transvascular aortic valve replacement with self expanding stent-valve device." Poster from the presentation given at SMIT 2000, 12th International Conference. Sep. 5, 2000.
Hijazi, Z.M. "Transcatheter Valve Replacement: A New Era of Percutaneous Cardiac Intervention Begins." *J. of Am. College of Cardio.* 2004; 43(6): 1088-1089.
Huber, C.H. et al. "Do valved stents compromise coronary flow?" *European Jouranl of Cardio-thoracic Surgery.* 2004; vol. 25: 754-759.
Knudsen, L. L. et al. "Catheter-implanted prosthetic heart valves." *Int'l J. of Art. Organs.* 1993; 16(5): 253-262.
Kort, S. et al. "Minimally invasive aortic valve replacement: Echocardiographic and clinical results." *Am. Heart J.* 2001; 142(3): 476-481.
Love, C. et al. "The Autogenous Tissue Heart Valve: Current Status." *Journal of Caridac Surgery.* 1991; 6(4): 499-507.
Lutter, G. et al. "Percutaneous aortic valve replacement: An experimental study. I. Studies on implantation." *J. of Thoracic and Cardio. Surg.* 2002; 123(4): 768-776.
Moulopoulos, S. D. et al. "Catheter-Mounted Aortic Valves." *Annals of Thoracic Surg.* 1971; 11(5): 423-430.
Paniagua, D. et al. "Percutaneous heart valve in the chronic in vitro testing model." *Circulation.* 2002; 106: e51-e52.
Paniagua, D. et al. Heart Watch (2004). *Texas Heart Institute.* Spring, 2004 Edition: 8 pages.
Pavcnik, D. et al. "Percutaneous bioprosthetic venous valve: A long-term study in sheep." *J. of Vascular Surg. 2002*; 35(3): 598-603.
Phillips, S. J. at al. "A Temporary Catheter-Tip Aortic Valve: Hemodynamic Effects on Experimental Acute Aortic Insufficiency." *Annals of Thoracic Surg.* 1976; 21(2): 134-136.
Sochman, J. et al. "Percutaneous Transcatheter Aortic Disc Valve Prosthesis Implantation: A Feasibility Study." *Cardiovasc. Intervent. Radiol.* 2000; 23: 384-388.
Stuart, M. "In Heart Valves, A Brave, New Non-Surgical World." *Start-Up.* 2004: 9-17.
Vahanian, A. et al. "Percutaneous Approaches to Valvular Disease." *Circulation.* 2004; 109: 1572-1579.
Van Herwerden, L. A. et al., "Percutaneous valve implantation: back to the future?" *Euro. Heart J.* 2002; 23(18): 1415-1416.
Zhou, J. Q. et al. "Self-expandable valved stent of large size: off-bypass implantation in pulmonary position." *Eur. J. Cardiothorac.* 2003; 24: 212-216.
Fawzi, et al., U.S. Appl. No. 11/155,309, entitled "Apparatus and methods for intravascular embolic protection," filed Jun. 16, 2005 (WSGR Reference No. 30207-719.201.
Salahieh, et al., U.S. Appl. No. 11/232,441, entitled "Methods and apparatus for endovascular heart valve replacement comprising tissue grasping elements," filed Sep. 20, 2005 (WSGR Reference No. 30207-702.503).
Salahieh, et al., U.S. Appl. No. 11/232,444, entitled "Methods and apparatus for endovascular heart valve replacement comprising tissue grasping elements," filed Sep. 20, 2005 (WSGR Reference No. 30207-702.504).

Salahieh, et al., U.S. Appl. No. 11/274,889, entitled "Medical implant deployment tool," filed Jun. 16, 2005 (WSGR Reference No. 30207-718.201).

Salahieh, et al., U.S. Appl. No. 11/275,913, entitled "Two-Part Package for Medical Implant," filed Feb. 2, 2006 (WSGR Reference No. 30207-723.201).

Salahieh, et al., U.S. Appl. No. 11/314,183, entitled "Medical Device Delivery," filed Dec. 20, 2005 (WSGR Reference No. 30207-725.201).

Salahieh, et al., U.S. Appl. No. 11/314,969, entitled "Methods and Apparatus for Performing Valvuloplasty," filed Dec. 20, 2005 (WSGR Reference No. 30207-727.201).

Salahieh, et al., U.S. Appl. No. 12/132,304 entitled "Low profile heart valve and delivery system," filed Jun. 3, 2008.

Haug et al.; U.S. Appl. No. 12/492,512 entitled "Everting Heart Valve," filed Jun. 26, 2009.

Paul et al.; U.S. Appl. No. 12/578,463 entitled "Medical Devices and Delivery Systems for Delivering Medical Devices," filed Oct. 13, 2009.

Paul et al.; U.S. Appl. No. 12/578,447 entitled "Medical Devices and Delivery Systems for Delivering Medical Devices," filed Oct. 13, 2009.

* cited by examiner

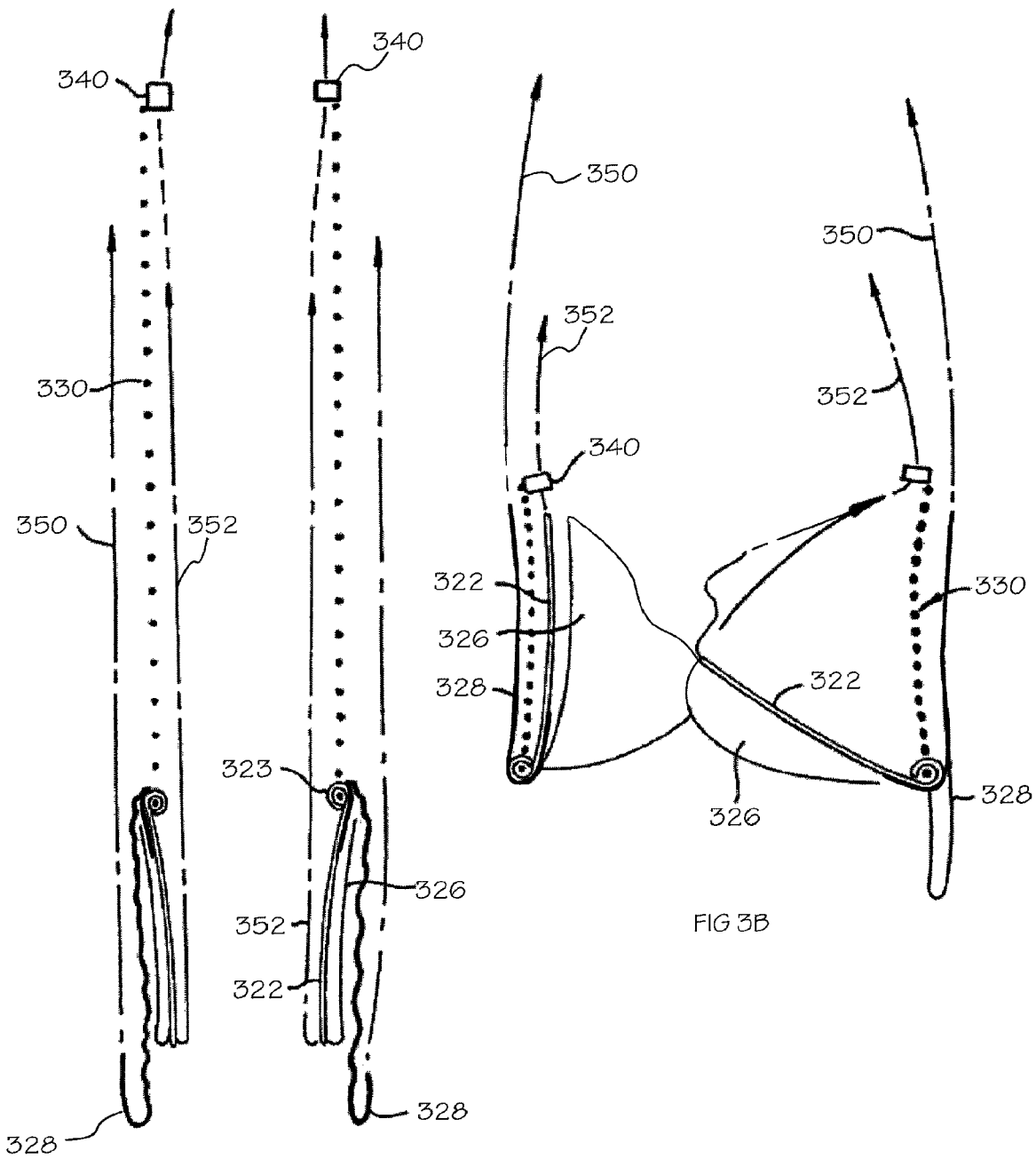

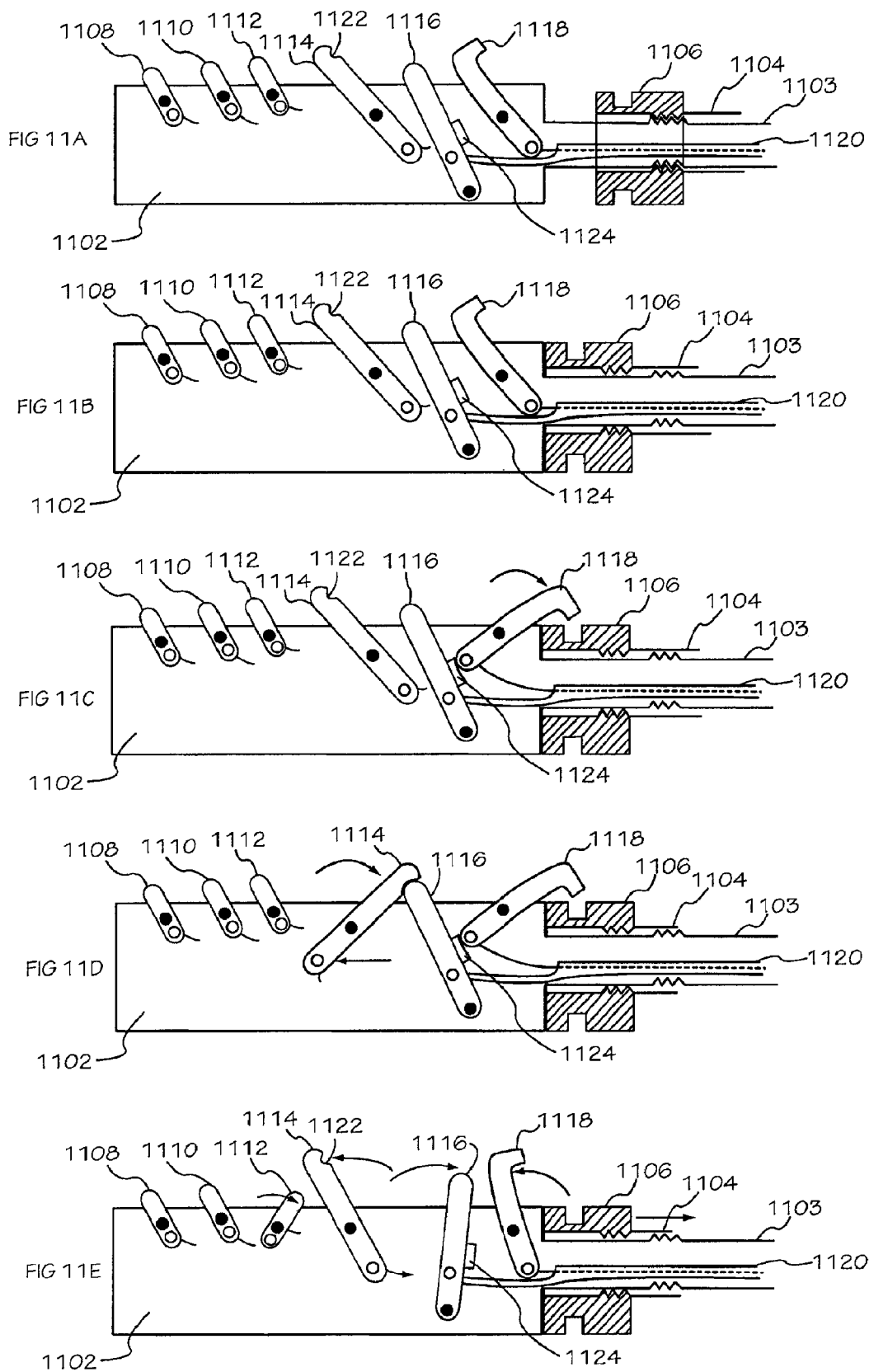

MEDICAL IMPLANT DELIVERY AND DEPLOYMENT TOOL

CROSS-REFERENCE

This application is a continuation-in-part application of U.S. patent application Ser. No. 10/982,388, filed Nov. 5, 2004, which is a continuation-in-part application of U.S. patent application Ser. No. 10/746,120, filed Dec. 23, 2003 now abandoned, and is a continuation-in-part application of U.S. patent application Ser. No. 10/870,340, filed Jun. 16, 2004, which applications are incorporated herein by reference in their entirety and to which applications we claim priority under 35 USC §120.

BACKGROUND OF THE INVENTION

The invention relates generally to medical implant systems. In particular, the invention relates to a tool to endovascularly deliver and deploy a medical implant, such as a replacement heart valve. Aspects of the invention may also be used to deliver and deploy other medical implants and to deliver those implants percutaneously, endoscopically, laparoscopically, etc.

Medical devices may be implanted within patients' bodies for a variety of medical purposes. Many implants can be delivered in a minimally invasive manner, such as through percutaneous access to the patient's vasculature, through an existing orifice, etc. For example, replacement heart valves may be endovascularly delivered to a patient's heart, as described in more detail in U.S. patent application Ser. No. 10/982,388; U.S. patent application Ser. No. 10/746,120, filed Dec. 23, 2003; and U.S. patent application Ser. No. 10/870,340, filed Jun. 16, 2004. Multiple implant operations may need to be performed during the minimally invasive delivery and deployment of a medical implant; the prior art is replete with handles and actuators for these purposes.

Replacement heart valves may be delivered endovascularly to the patient's heart from an entry point far from the patient's heart. For example, replacement aortic valves can be delivered retrograde (i.e., against the blood flow) from an insertion point near the patient's groin through the femoral artery and the aorta. Any physician-operated actuators used to deliver, deploy, retrieve or otherwise operate the replacement valve or its components must perform their operations over this distance. In addition to any expansion of the valve and/or anchor from a deployment shape or self-expanded shape to a deployed shape, these operations may include expansion of the replacement valve against the inward force of the tissue in and around the patient's native valve. Each of these operations could require the delivery of an expansion force from the external actuator to the implant. Other possible valve replacement procedure operations controlled by external actuators include detachment of the delivery tool from the implant after a successful placement procedure, collapsing and moving an implant to a more desirable implant location, and retrieval of the implant back into a delivery tool catheter or sheath.

SUMMARY OF THE INVENTION

The invention provides a medical implant and implant deployment tool and methods of use. One aspect of the invention provides an apparatus for endovascularly replacing a patient's heart valve, with the apparatus including a replacement heart valve implant comprising a valve and an expandable anchor; and a deployment tool adapted to endovascularly deliver the replacement heart valve implant to an implant site within the patient, the deployment tool comprising an actuator adapted to exert an axially directed force on the anchor. In some embodiments, the deployment tool is adapted to provide a force of 5 to 35 pounds from the actuator to the anchor and/or a mechanical advantage of at least 2:1 from the actuator to the anchor. The mechanical advantage may be variable over a movement range of the actuator.

In some embodiments, the implant also includes a lock, the deployment tool being adapted to operate the lock to maintain the implant in an expanded configuration. This operation may be performed by either controlling the locking or unlocking of the lock, or both. In some embodiments, the actuator includes an anchor actuator, the deployment tool further having a sheath and a sheath actuator adapted to move the sheath with respect to the anchor. In some embodiments, the actuator includes an anchor actuator, with the deployment tool further having an unlocking actuator adapted to unlock the anchor from a locked configuration. In some embodiments, the actuator includes an anchor actuator, with the deployment tool further including a valve actuator adapted to move the valve with respect to the anchor, and, optionally, a nosecone actuator adapted to move a nosecone with respect to the anchor.

In some embodiments the deployment tool further includes an anchor actuation element operably connecting the actuator with the anchor, the actuator and anchor actuation element being adapted to provide movement of a distal end of the anchor actuation element at a variable speed as the actuator moves at a constant speed. In some embodiments, the deployment tool further includes a feedback mechanism providing information indicating a deployment state of the implant.

In some embodiments the deployment tool further includes a plurality of actuators each adapted to perform a different deployment operation. The deployment tool may also include an actuator interlock adapted to prevent operation of one of the actuators before operation of another of the actuators. The actuators may also be arranged on the deployment tool in a preferred order of operation. For example, in some embodiments the actuator includes an anchor actuator, with the deployment tool further including a sheath, a sheath actuator adapted to move the sheath with respect to the anchor, an implant attachment element adapted to attach the implant to the deployment tool, and a release actuator adapted to detach the attachment element from the implant, with the anchor actuator being disposed between the sheath actuator and the release actuator on the deployment tool. In some embodiments one actuator may also be adapted to operate the plurality of actuation elements, perhaps sequentially. The actuator may also include a power source, such as a solenoid, motor, hydraulic or pneumatic cylinder, etc. A clutching mechanism may also be provided to limit a force transmitted from an actuator to an implant.

Another aspect of the invention provides a method for endovascularly replacing a heart valve of a patient, with the method including the following steps: endovascularly delivering a replacement heart valve implant having a valve and an anchor to an implant site within the patient; and applying an axially directed force from an actuator outside of the patient to the anchor. Some embodiments include one or more of the following steps: using an actuator to move a sheath with respect to the anchor; using an actuator to release the anchor from the deployment tool; using an actuator to lock the anchor in an expanded configuration; using an actuator to unlock the anchor from a locked configuration; using an actuator to move the replacement valve with respect to the anchor; and/or applying an outward pressure from expansion of the anchor to the implant site of at least about 7 psi.

In some embodiments of the method, the actuator provides a mechanical advantage of at least about 2:1, and the mechanical advantage may vary over an actuator movement range. In some embodiments, an anchor actuation element operably connects the actuator with the anchor, and the applying step includes moving a distal end of the anchor actuation element at a variable speed as the actuator moves at a constant speed. Some embodiments also provide the step of providing information about completion of actuation through a feedback mechanism.

In some embodiments, the applying step includes the step of applying the expansion force with a first actuation element, with the method further including the step of performing a second replacement valve deployment operation using a second actuation element. In some embodiments, the actuator interfaces with the first and second actuation elements. Some embodiments also include the step of operating an actuator interlock before operating the second actuation element. In some embodiments, the actuator is a first actuator, with the performing step including the step of performing the second replacement valve deployment operation with a second actuator. Some embodiments further include the step of performing a third replacement valve deployment operation with a third actuator, wherein the actuators are arranged in an operation order, the method further comprising the step of operating the actuators in the operation order.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3A and 3B are schematic views of an implant and part of a deployment tool according to yet another embodiment of this invention.

FIGS. 11A-11E are schematic views of part of an implant deployment tool according to another embodiment of the invention showing deployment actuators.

DETAILED DESCRIPTION OF THE INVENTION

Figure 1:
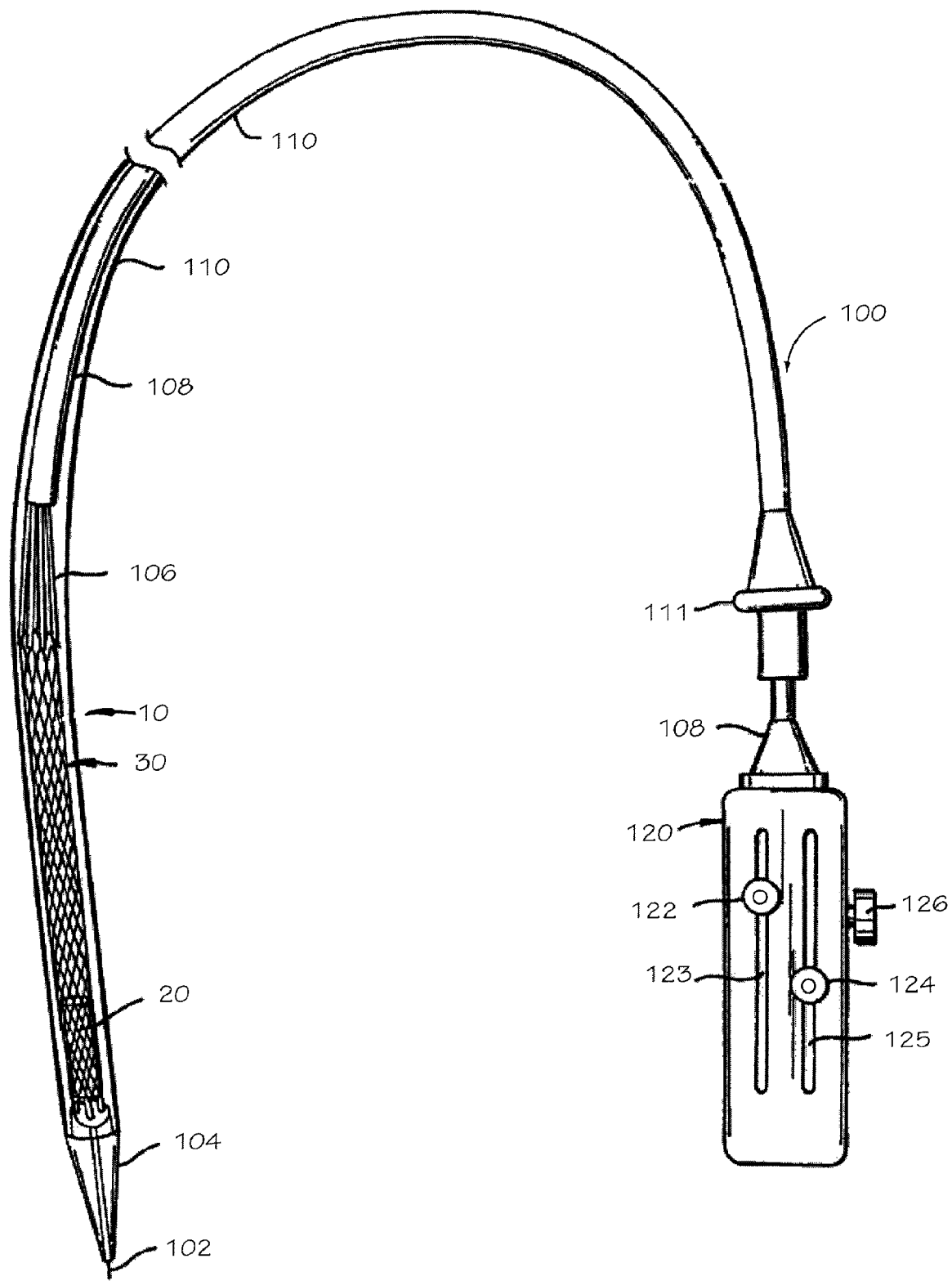
FIG. 1 is a partial cross-sectional view of an implant and deployment tool according to an embodiment of this invention.

The medical implant deployment tool of this invention may be used to deliver, deploy, implant, release, retrieve and otherwise actuate a medical implant. FIG. 1 shows one embodiment of an implant 10 and deployment tool 100. In this embodiment, the implant is a replacement heart valve incorporating a valve 20 and an anchor 30 (such as a braided stent) designed to be delivered to the patient's heart endovascularly from an opening in the patient's femoral artery. Deployment tool 100 supports implant 10 at least in part via actuation elements 106 disposed at the distal end of a delivery catheter 108 within an outer sheath 110. A handle 120 is connected to delivery catheter 108 at its proximal end. A nosecone 104 (which may be collapsible) extends from the distal end of sheath 110 as the implant 10 and sheath 110 are advanced through the patient's vasculature to the patient's heart over a guidewire 102.

Deployment tool 100 also has actuators and other user controls at its proximal end for use by a physician during the implant procedure. For example, located in handle 120 are slidable actuators 122 and 124 disposed in tracks 123 and 125, respectively, as well as a rotating actuator 126. Actuators 122, 124 and 126 may be connected to actuation elements (not shown) used to perform implant deployment operations. One such operation (by moving, e.g., actuator 122 within handle 120) draws the distal end of anchor 30 proximally with respect to the anchor's proximal end, while actuation elements 106, delivery catheter 108 and handle 120 provide a countervailing force on the anchor's proximal end. This axially directed anchor expansion force may be between about 5 pounds and about 35 pounds, with the expanding anchor providing outward pressure on the patient's tissue at the implant site of between about 7 psi and about 28 psi. In addition, a circumferential handle actuator 111 is provided on sheath 110 to move delivery catheter 108, which is connected to handle 120, with respect to sheath 110. This relative movement may be used, e.g., to apply an axially directed force by the sheath on the proximal end of anchor 30 to resheath the anchor and valve. In some embodiments, this resheathing force may be between about 5 pounds and about 35 pounds.

Figure 2:
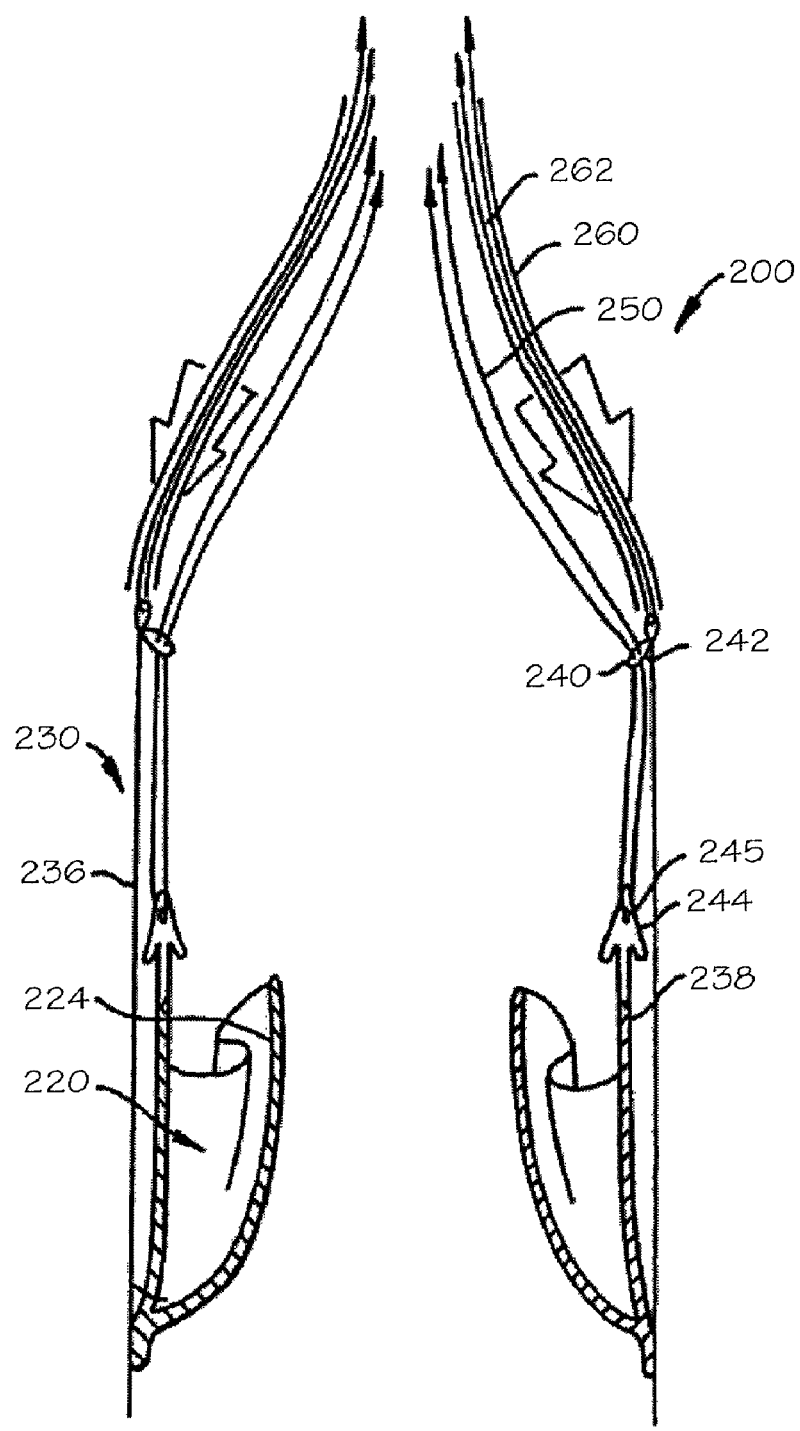
FIG. 2 is a cross-sectional view of an implant and part of a deployment tool according to another embodiment of this invention.

FIG. 2 illustrates certain implant deployment operations performed by a deployment tool. The implant in this embodiment is a replacement heart valve with a valve element 220 supported within a radially expandable anchor 230. In this embodiment, anchor 230 may be expanded radially by applying an axially directed force to foreshorten the anchor. The axially directed force is applied on the distal end of anchor 230 by pulling valve support post 238 proximally using deployment tool actuation elements 250 (such as threads or control wires) that pass through eyelets 245 formed in the arrowhead shaped locking elements 244 of posts 238. While the posts are pulled proximally, a countervailing axially directed force is applied to the proximal end of anchor 230 by axially stiff deployment tool actuation elements 260. This axially directed anchor expansion force may be between 5 pounds and about 35 pounds, with the expanding anchor providing outward pressure on the patient's tissue at the implant site of between about 7 psi and about 28 psi. Foreshortening concludes when locking elements 244 pass into buckle-shaped locking elements 240. The deployment tool may be detached from the implant by, e.g., releasing one end of actuation elements 250 and pulling the free end through eyelets 245, and releasing one end of attachment elements 262 and pulling their free ends through the anchor attachment sites 242 (e.g., closed cells at the proximal end of a braided stent) to release actuation elements 260 from anchor 230. Movement of the actuation elements and attachment elements may be controlled using deployment tool actuators (not shown) located on the exterior of the patient.

FIGS. 3A and 3B show another embodiment of a replacement heart valve implant and parts of its deployment tool. FIG. 3A shows the implant and deployment tool in a delivery configuration in which a valve 326, its support posts 322 and a seal 328 extend distally of a radially expandable anchor 330. During deployment, axially directed forces are applied on the implant via deployment tool actuation elements 350 and 352 to foreshorten and expand anchor 330, to rotate posts 322 to their deployed position, and to place seal 328 on the outside of anchor 330, as shown in FIG. 3B. Locking elements (not shown) on the free ends of posts 322 interact with locking elements 340 on the proximal end of anchor 330 to lock anchor 330 in its expanded configuration. As in the other embodiments, movement of actuation elements 350 and 352 may be controlled using deployment tool actuators (not shown) located on the exterior of the patient.

Figure 4A:
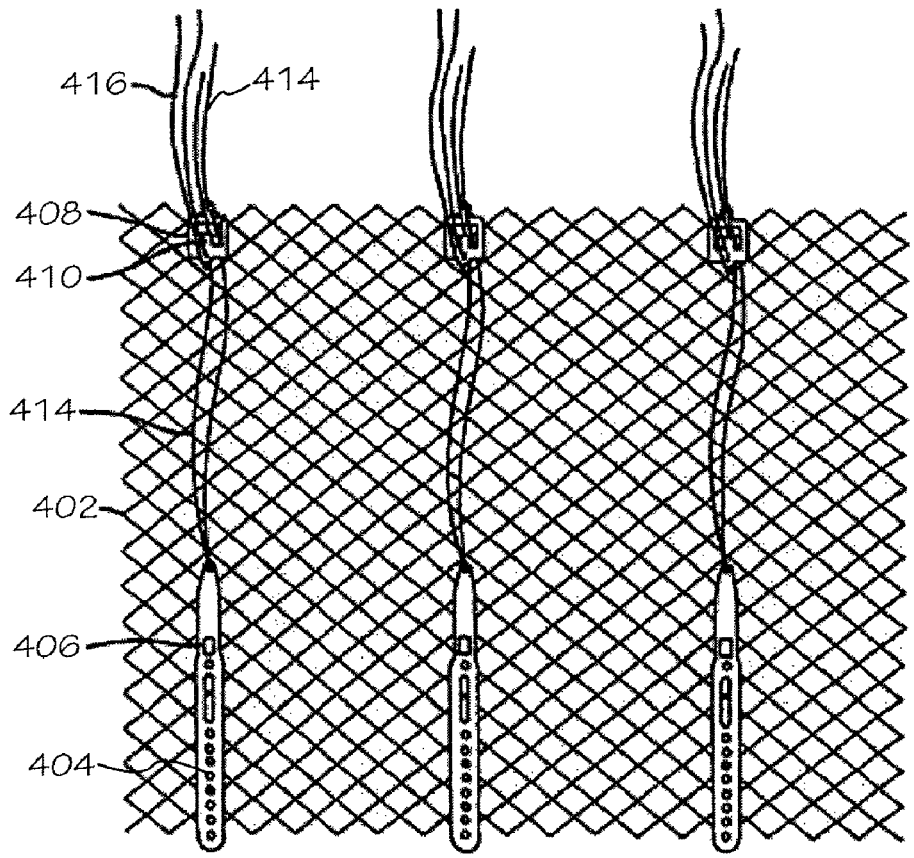
FIGS. 4A and 4B are elevational views of part of an implant and part of a deployment tool according to still another embodiment of this invention, with the implant being cut open and laid flat for viewing purposes.
Figure 4B:
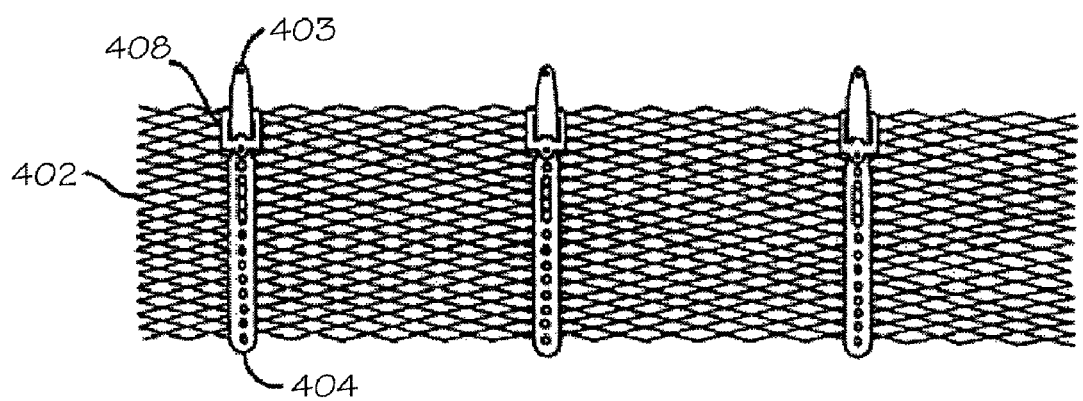

FIGS. 4A and 4B show yet another embodiment of a medical implant and part of its deployment tool. The implant may be, e.g., the anchor portion of a replacement heart valve, similar to those described above. For visualization purposes, braided anchor 402 has been opened and flattened in FIGS. 4A and 4B. Locking posts 404 (which may be used to support a replacement heart valve within anchor 402) are attached to the distal end of anchor 402, and buckle-shaped locking elements 408 are attached to the proximal end. Actuation elements 414 passing through locking elements 408 and attached to holes 403 formed in the proximal ends of posts 404 may be used to apply an axially directed force on the distal end of anchor 402 (against a countervailing force applied to the proximal end of anchor 402 by other actuation elements, not shown) to foreshorten and radially expand the anchor from the delivery configuration shown in FIG. 4A to the locked and deployed configuration shown in FIG. 4B. When locked, locking tabs 410 formed in locking elements 408 mate with corresponding holes 406 formed in posts 404. In this embodiment, the anchor may be unlocked by pulling an unlocking actuation element 416 proximally. This movement removes tabs 410 from holes 406, thereby releasing posts 404 and permitting anchor 402 to elongate and radially shrink, thereby enabling the implant to be moved within the patient or removed from the patient. If, however, the anchor is to remain locked and the implant is to remain in the patient, deployment tool actuation elements 414 and 416 may be detached from the implant by releasing one end and pulling the free end through. Movement of deployment tool actuation elements 414 and 416 may be controlled using deployment tool actuators (not shown) located on the exterior of the patient.

Figure 5:
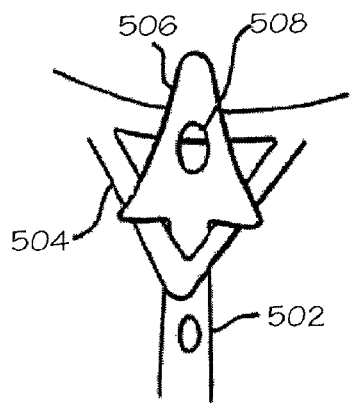
FIG. 5 is an elevational view of a locking mechanism for an implant.

FIG. 5 shows details of a locking mechanism for a medical implant, such as a replacement heart valve with a radially expandable anchor as described above. A locking element 506 formed at the proximal end of a post 502 (such as a valve support post) interacts with a locking element 504 formed in or attached to the proximal end of an anchor. A hole 508 is formed in the proximal end of post 502 for use with a deployment tool actuation element (not shown).

Figure 6:
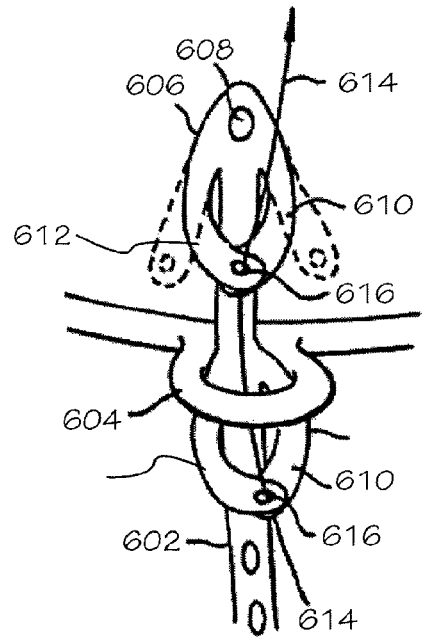
FIG. 6 is an elevational view of another locking mechanism for an implant and part of a deployment tool.

FIG. 6 shows another embodiment of a locking mechanism for a medical implant, such as a replacement heart valve with a radially expandable anchor as described above. In this embodiment, the anchor has multiple locking positions corresponding to multiple deployed diameters. Thus, the implant's post 602 (which may also be used, e.g., as a valve support) has multiple locking elements 606 with bendable arms 610 and 612. In the state shown in solid lines in FIG. 6, as the post 602 is pulled proximally toward and through anchor locking element 604 (via, e.g., a deployment tool actuation element passing through hole 608 in post 602) the anchor locks are restrained by a lock actuator 614 passing through holes 616 formed in arms 610 and 612, allowing the post locking elements 606 to pass through the anchor locking element 604 without engaging. This feature permits the user to visualize the location of the implant and to maneuver the implant within the patient before finally deploying the implant. By pulling lock actuator 614 free of holes 616, however, the resilient or shape memory action of arms 610 and 612 enables the arms to move to the position shown in phantom in FIG. 6, thereby enabling the post locking element to lock with the anchor locking element. As with the other embodiments, movement of deployment tool actuation element 614 may be controlled using deployment tool actuators (not shown) located on the exterior of the patient.

Figure 7:
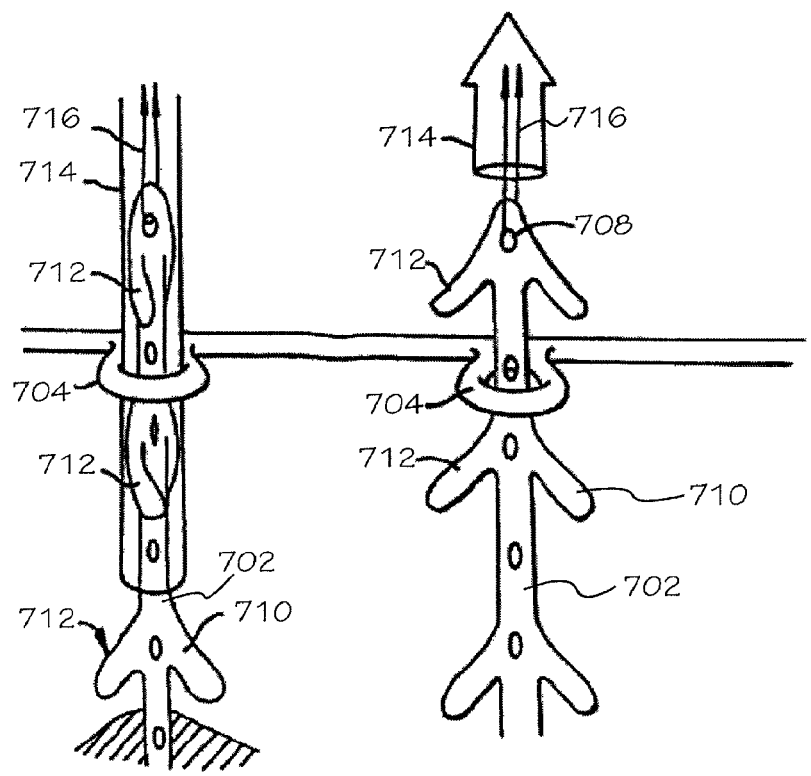
FIG. 7 is an elevational view of yet another locking mechanism for an implant and part of a deployment tool.

FIG. 7 shows yet another embodiment of a multiple position locking mechanism for a medical implant (such as a replacement heart valve with radially expandable anchor). As in the embodiment shown in FIG. 6, post 702 (which may be a valve support post) has multiple locking elements, each with bendable arms 710 and 712. In this embodiment, the post may be drawn proximally into an anchor locking element 704 by pulling proximally on deployment tool actuation element 716 passing through a hole 708 formed in the proximal end of the post. In the deployment configuration shown in the left side of FIG. 7, as the post is drawn proximally toward locking element 704, the bendable locking element arms 710 and 712 are restrained by an actuation element 714 shaped like an overtube that passes through locking element 704. When locking is to be permitted (e.g., after confirmation of implant location, procedure safety and efficacy, etc.), actuation element 714 may be drawn proximally to permit arms 710 and 712 to assume their locking positions, as shown on the right side of FIG. 7. As with the other embodiments, movement of deployment tool actuation elements 714 and 716 may be controlled using deployment tool actuators (not shown) located on the exterior of the patient.

Figure 8A:
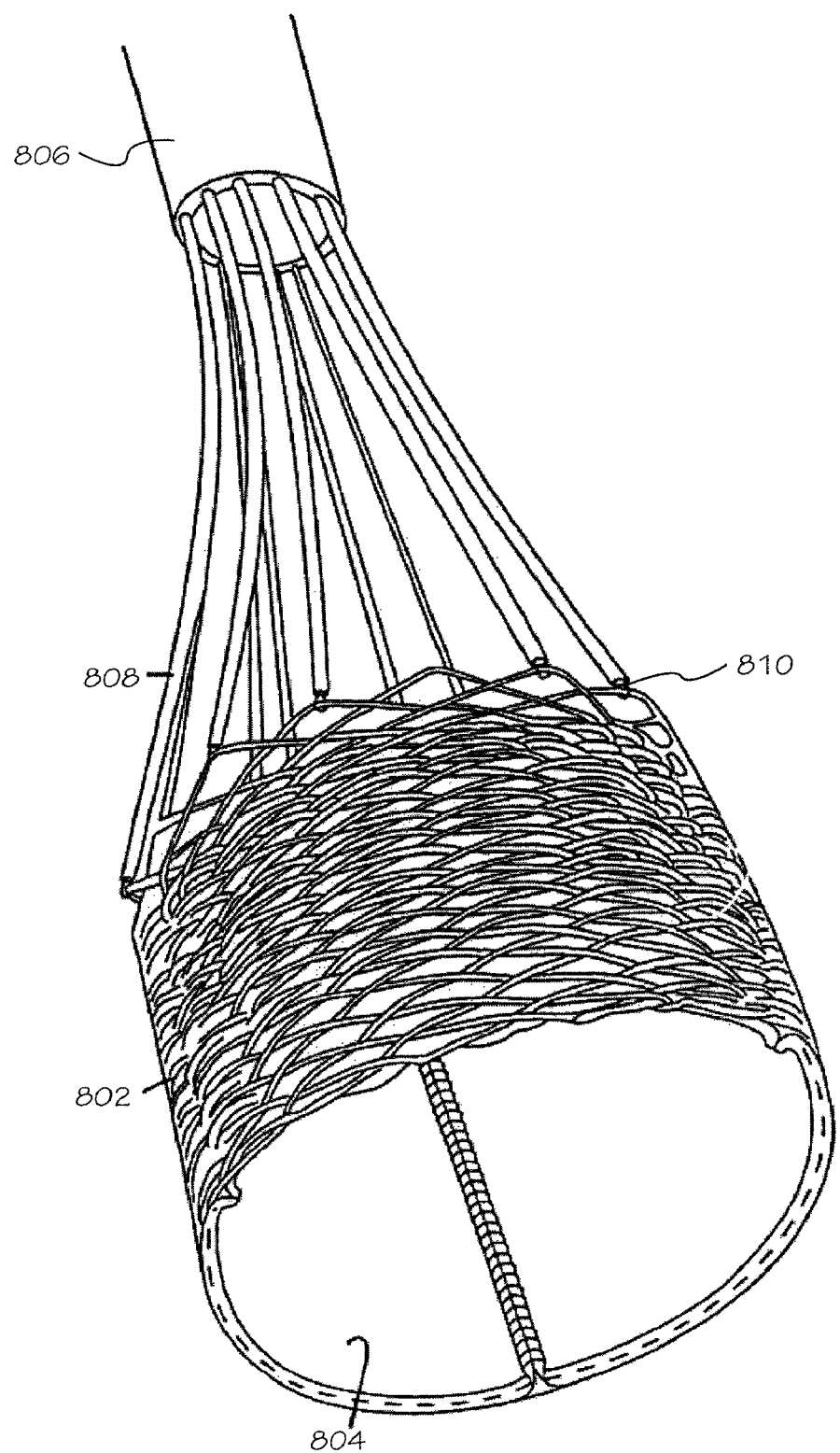
FIG. 8A is a perspective view of an implant and part of a deployment tool according to an embodiment of this invention.
Figure 8B:
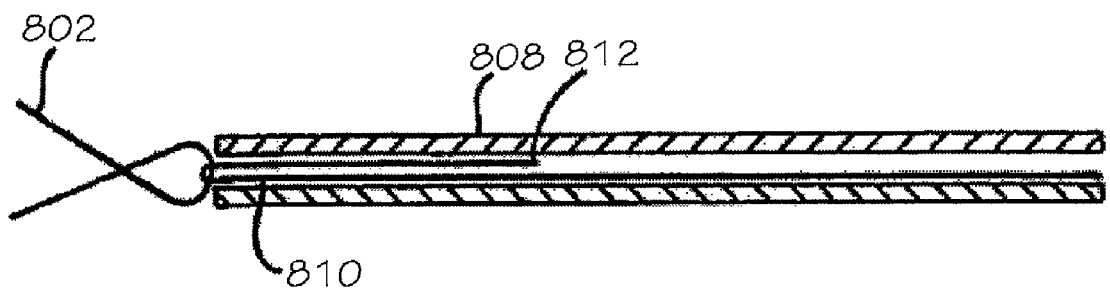
FIGS. 8B-8D are cross-sectional views of a release mechanism for the implant and deployment tool of FIG. 8A.
Figure 8C:
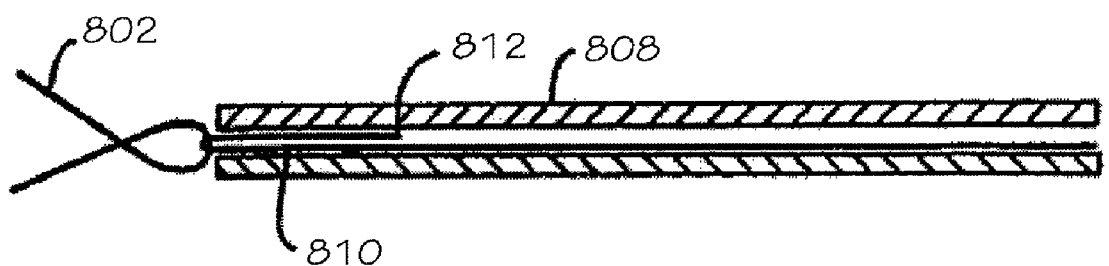
Figure 8D:
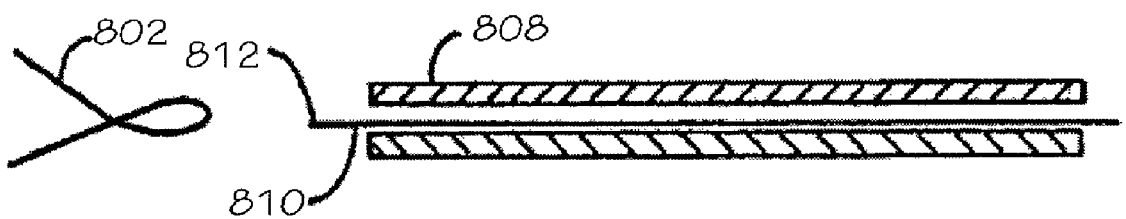

FIGS. 8A-8D illustrate one embodiment of an implant release mechanism. FIG. 8A shows a replacement heart valve implant with a valve 804 supported within an anchor 802. The implant is attached to a deployment tool via attachment elements 810 and actuation elements 808 extending from a distal end of a delivery catheter 806. As shown in FIGS. 8B-8D, to release anchor 802 from the deployment tool, attachment element 810 may be moved proximally with respect to the actuation element 808 to pull its free end 812 through the closed cell of anchor 802. This movement may be controlled, e.g., by an actuator (not shown) on the exterior of the patient.

Figure 9:
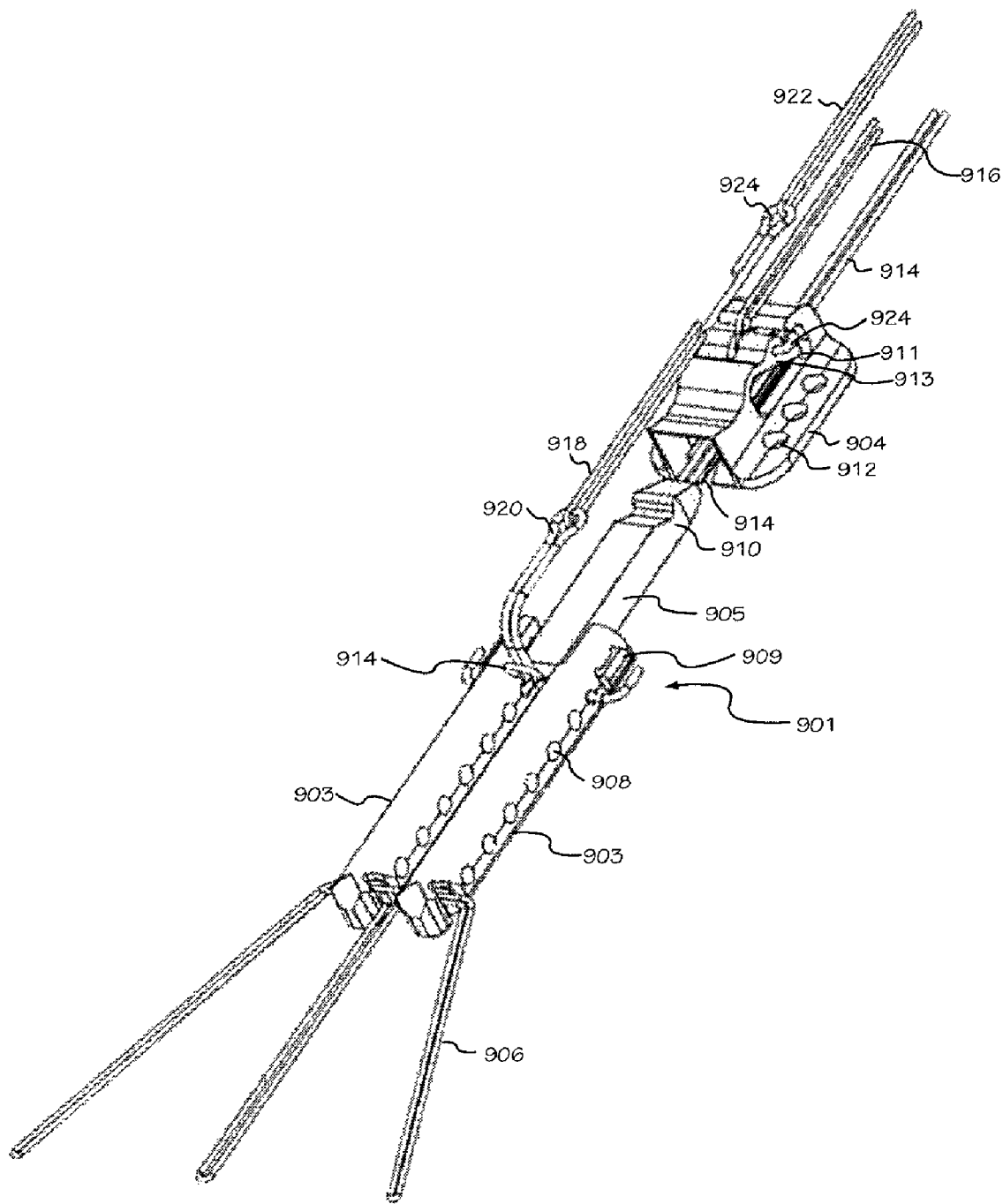
FIG. 9 is a perspective view of a locking mechanism for an implant and part of a deployment tool according to yet another embodiment of the invention.

FIG. 9 is a perspective view of a locking mechanism for an implant and part of a deployment tool according to yet another embodiment of the invention. In this embodiment, post 901 (such as a post used to lock a radially expandable medical implant anchor and optionally to support a valve within the anchor) is attached to an anchor (not shown) by looped threads 906. In this embodiment, post 901 has valve support elements 903 and a locking element 905 whose position with respect to support elements 903 may be adjusted. In an alternate embodiment, elements 903 and 905 may be formed of a single piece of material. Arms 909, on locking element 905, help hold locking element 905 and support elements 903 in place. Holes 908 formed in support elements 903 may be used to attach a valve to the post. A tooth 910 formed on the proximal end of locking element 905 serves as a locking element interacting with a corresponding detent 911 on a lever arm 913 on an anchor locking element 904, which may be attached to the anchor by sutures or threads passing through holes 912. To foreshorten and radially expand the anchor to which post 901 and locking element 904 are attached, an axially directed force is applied to the anchor by applying a proximally directed force on post 901 via deployment tool actuation element 914 (which passes through post 901 and around a release pin 920) while providing a countervailing axially directed force on the proximal end of the anchor. Insertion of tooth 910 into locking element 904 locks the anchor in an expanded configuration. The anchor may be unlocked by pulling proximally and radially in on an unlocking actuator 916 (which passes around a release pin 924), which moves detent 911 of locking element 904 away from the tooth 910 of post 901. If, however, the user wishes to maintain the locked configuration, actuation elements 914 and 916 may be detached by pulling on release actuation elements 918 and 922 to remove release pins 920 and 924, respectively. As in the other embodiments, movement of actuation elements 914, 916, 918 and 922 may be controlled by actuators located exterior to the patient.

Figure 10A:
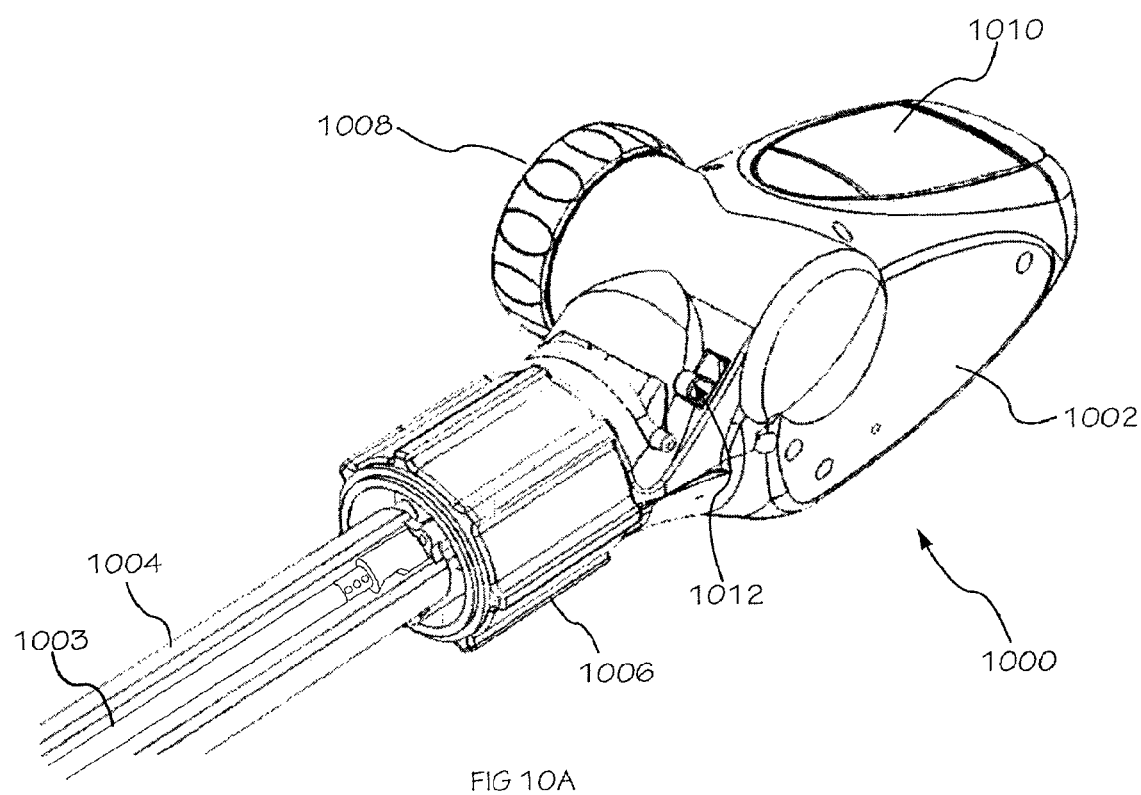
FIGS. 10A-10C are perspective views of part of an implant deployment tool according to an embodiment of the invention showing deployment tool actuators.
Figure 10B:
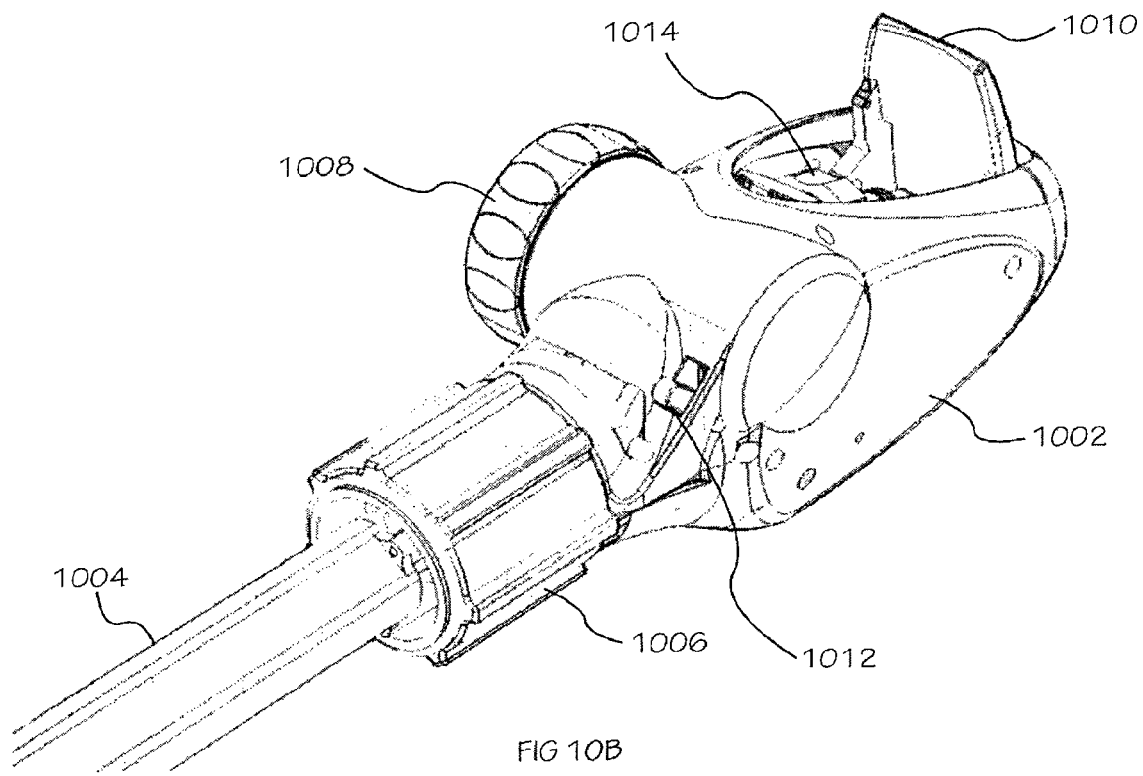
Figure 10C:
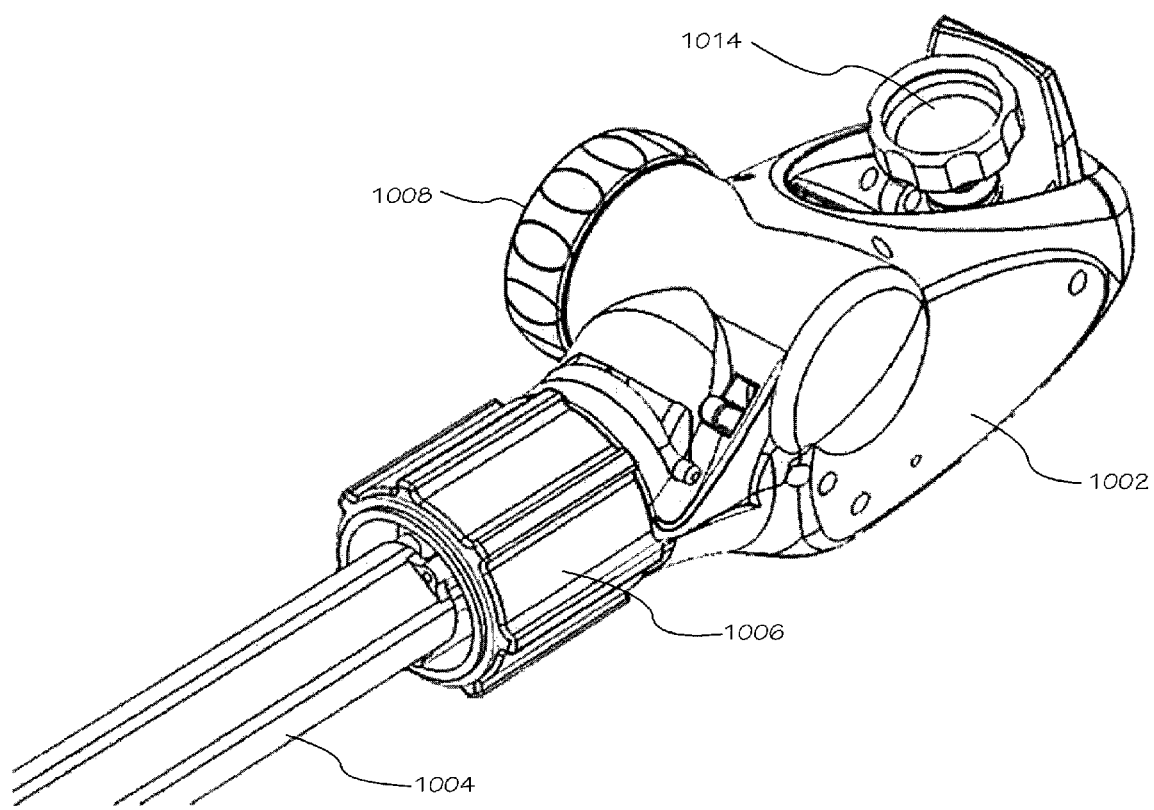

FIGS. 10A-10C show details of deployment tool actuators according to one embodiment of the invention. Deployment tool 1000 may be used, e.g., to endovascularly deliver and deploy a medical implant, such as a replacement heart valve. Deployment tool handle 1002 supports a plurality of actuators, such as a rotating actuator 1006 controlling movement of a sheath 1003 (located within a handle extension 1004) and a rotating actuator 1008 which may be used, e.g., to apply an axially directed force on posts of a replacement heart valve anchor through actuation elements (not shown) extending through sheath 1003. The rotating actuators may provide mechanical advantage to the implant deployment operations. For example, sheath actuator 1006 may be used to move sheath 1003 distally with respect to the implant to resheath the implant. The axially directed force required to resheath the implant may be between, e.g., about 5 pounds and about 35 pounds. To facilitate this operation, actuator 1006 and its associated gear connection to the sheath (e.g., rack and pinion gears) are designed to provide a mechanical advantage of at least about 2:1.

In some deployment operations, it may be important to ensure that certain deployment steps are performed before other deployment steps, some of the actuators may be configured and arranged such that they cannot be operated before other actuators have been operated or until other actuators are in a particular position. In this embodiment, for example, one of the actuators is formed as an access door 1010. Actuator 1010 maybe used, e.g., to release an anchor lock prevention mechanism, thereby finalizing the implant deployment operation. Movement of actuator 1010 provides access to another actuator, rotating actuator 1014, which may then be used to release the actuation elements (e.g., the actuation elements transmitting the axially directed forces to the anchor, the anchor lock prevention mechanism, etc.) from the implant.

FIGS. 11A-11E show another embodiment of a medical implant deployment tool for, e.g., delivery and deployment of a replacement heart valve, such as the valve embodiment shown in FIGS. 3A and 3B. A rotating actuator 1106 may be used to retract a sheath 1104 with respect to a delivery catheter 1103 via corresponding threads on the actuator and sheath as shown; the threads provide a mechanical advantage (of, e.g., 2:1) but may not be needed for the entire movement distance of the sheath, as shown. Also in this embodiment, the actuators 1108-1118 are arranged in a preferred order of operation and operate corresponding actuation elements (such actuation element 1120 connected to actuator 1114). For example, actuator 1118 may be used to rotate the posts 322 of FIG. 3 from the position shown in FIG. 3A to the position of FIG. 3B, and actuator 1116 may be used to move the posts from the position shown in FIG. 3B to that of FIG. 3A. Actuator 1114 may be used to pull the posts 322 (and therefore the distal end of anchor 330) proximally with respect to the proximal end of the anchor to expand the anchor. Actuator 1112 may be used to unlock the posts 322 from the buckle lock element 340, and actuators 1108 and 1110 may be used to release the implant from the delivery tool.

In addition, some of the actuators have features that prevent operation of one actuator until another actuator has been operated so that the implant deployment operations are performed in a desired order. For example, movement of actuator 1118 from the position shown in FIG. 11B to the position shown in FIG. 11C (to move the posts from the FIG. 3A position to the FIG. 3B position) brings one end of actuator 1118 into contact with a stop 1124 formed on actuator 1116, thereby preventing actuator 1116 (which moves the posts back to the FIG. 3A position) from moving until actuator 1118 is returned to its other position, as shown in FIG. 11E. In addition, a detent 1122 formed in actuator 1114 interacts with actuator 1116 as shown in FIG. 11D to prevent actuator 1116 from moving until actuator 1114 is moved again to provide slack in the actuation elements for movement of the posts, as shown in FIG. 11E.

Figure 12:
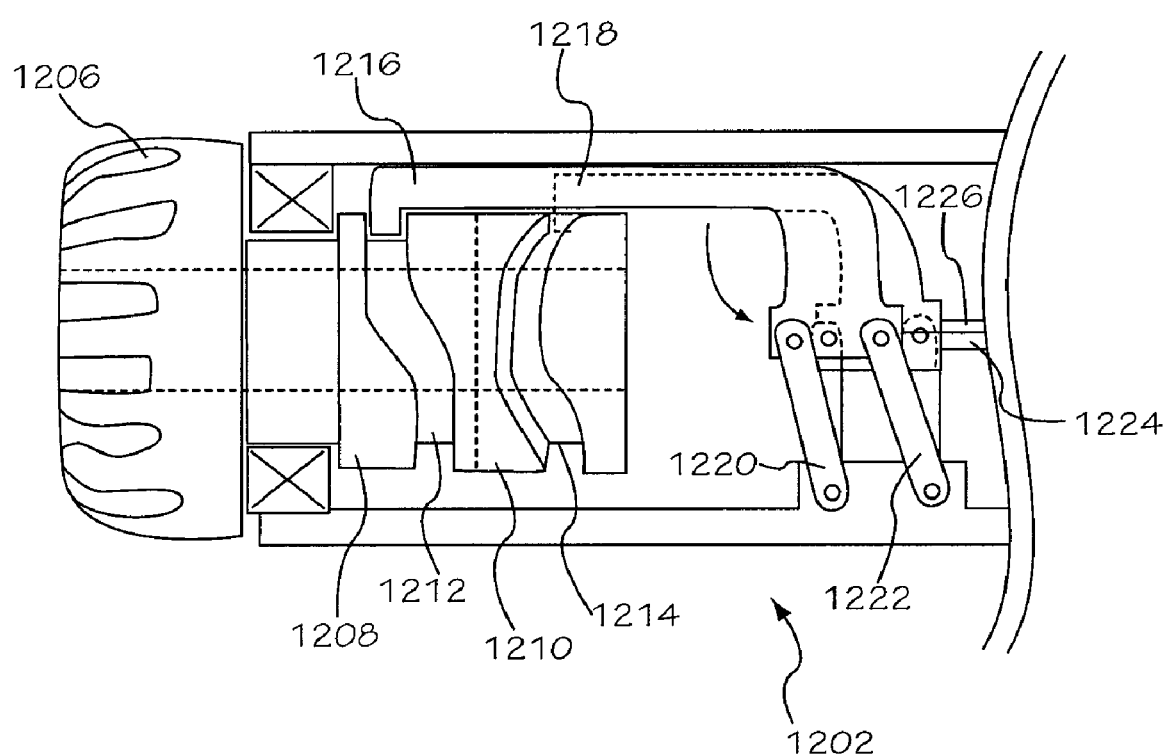
FIG. 12 is a schematic view of part of an implant deployment tool according to yet another embodiment of the invention showing a deployment actuator operating multiple actuation elements.

FIG. 12 shows an embodiment of a medical implant deployment tool in which a single actuator 1206 operates multiple actuation elements 1224 and 1226. The deployment tool may be used, e.g., to endovascularly deliver and deploy a medical implant, such as a replacement heart valve. Actuator 1206 extends from a proximal end of a deployment tool handle 1202. Rotation of actuator 1206 turns a spool 1208 within handle 1202. Actuation element arms 1216 and 1218 are supported within handle 1202 by linkages 1220 and 1222, respectively, and ride within grooves 1212 and 1214, respectively, formed in spool 1208. As spool 1206 turns, arms 1216 and 1218 move proximally and distally, thereby moving actuation elements 1224 and 1226 to perform implant deployment steps. The mechanical advantage provided by the actuator depends on the slope of grooves 1212 and 1214 and may change over the movement limits of the actuator, as in the embodiment shown in FIG. 12. In addition, the varying slope of grooves 1212 and 1214 provides for varying speed of actuation to, e.g., move one end of an expanding anchor at a varying speed as the actuator moves at a constant speed. Also, use of a single actuator ensures that the implant deployment steps will be performed in a particular order or otherwise in a synchronized fashion.

Figure 13:
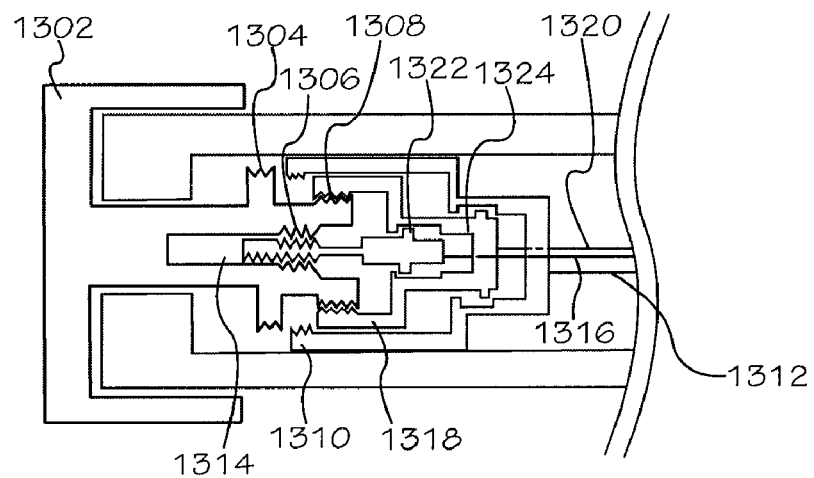
FIG. 13 is a schematic view of part of an implant deployment tool according to still another embodiment of the invention showing a deployment actuator operating multiple actuation elements at least partially sequentially.

FIG. 13 shows another embodiment of a medical implant deployment tool (used, e.g., to deliver and deploy a replacement heart valve) in which one actuator 1302 controls multiple actuation elements 1312, 1316 and 1320. As shown, threads 1306 of actuator 1302 mate with threads formed on a gear 1314 connected to actuation element 1316, and threads 1308 of actuator 1302 mate with threads formed on a gear 1318 connected to actuation element 1320. Rotation of actuator 1302 in the position shown in FIG. 13 draws gears 1314 and 1318, and actuation elements 1316 1320, proximally. A lip 1322 extending from gear 1314 travels within a groove 1324 formed in gear 1318 to limit the amount that gears 1314 and 1318, and therefore actuation elements 1316 and 1320, can move with respect to each other. In particular, when threads 1306 are engaged with the threads on gear 1314, but before threads 1308 have engaged the threads on gear 1318, gear 1314 and actuation element 1316 move independently of gear 1318 and actuation element 1320. When lip 1322 comes to the limit of its movement in groove 1324, however, gears 1314 and 1318 will move together, bringing threads 1308 into contact with the threads on gear 1318. A similar lip and groove arrangement is provided on gear 1318 and a third threaded gear 1310, which is connected to actuation element 1312, so that proximal movement of gear 1318 to the limit of the lip's movement within the groove causes gear 1318 to engage gear 1310 and the threads on gear 1310 to engage threads 1304 on actuator 1302. Thus, rotation of actuator 1302 moves actuation elements 1312, 1316 and 1320 in a synchronized fashion and ensures that the implant deployment steps will be performed in a particular order.

Figure 14:
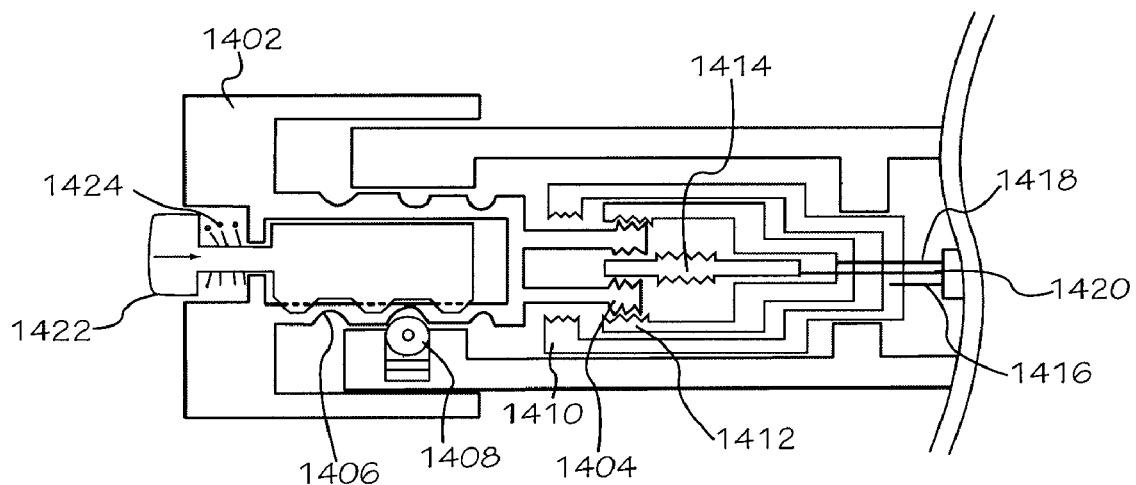
FIG. 14 is a schematic view of part of an implant deployment tool according to another embodiment of the invention showing a deployment actuator operating multiple actuation elements at least partially sequentially.

FIG. 14 shows yet another embodiment of a medical implant deployment tool (used, e.g., to deliver and deploy a replacement heart valve) in which one actuator 1402 controls multiple actuation elements 1416, 1418 and 1420. In the position shown in FIG. 14, threads 1404 of actuator 1402 mate with threads on gear 1412 connected to actuation element 1418. Rotation of actuator 1402 moves gear 1412 and actuation element 1418 linearly and can be used to apply an axially directed force (of, e.g., between about 5 pounds and about 35 pounds with a mechanical advantage of at least 2:1) on a medical implant (not shown) connected to actuation element 1418. To move actuator 1402 to a position in which the actuator can engage and control other actuation elements, spring-biased button 1422 can be depressed, which moves detent element 1408 out of the groove 1406 of actuator 1402, thereby enabling actuator 1402 to move forward or back. In the forward position (i.e., to the right as shown in FIG. 14), threads 1404 of actuator 1402 engage threads formed in gear 1414 which is connected to actuation element 1420. In the back position (i.e., to the left as shown in FIG. 14), threads 1404 of actuator 1402 engage threads formed in gear 1410, which is connected to actuation element 1416.

Figure 15:
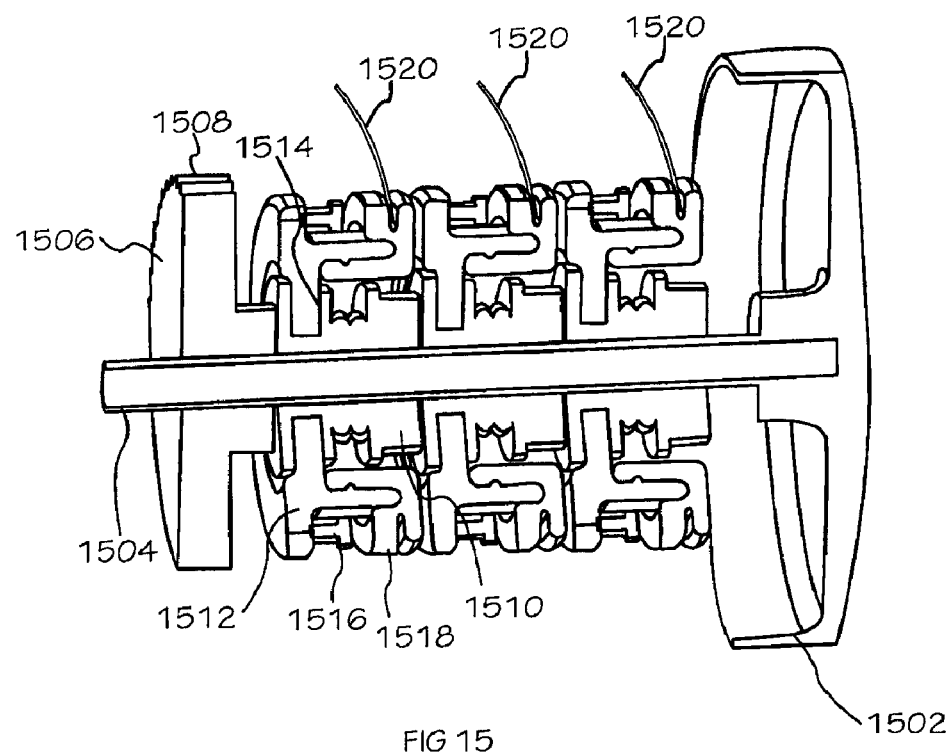
FIG. 15 is a cross-sectional view of part of an implant deployment tool according to yet another embodiment of the invention showing a deployment actuator operating multiple actuation elements.
Figure 16:
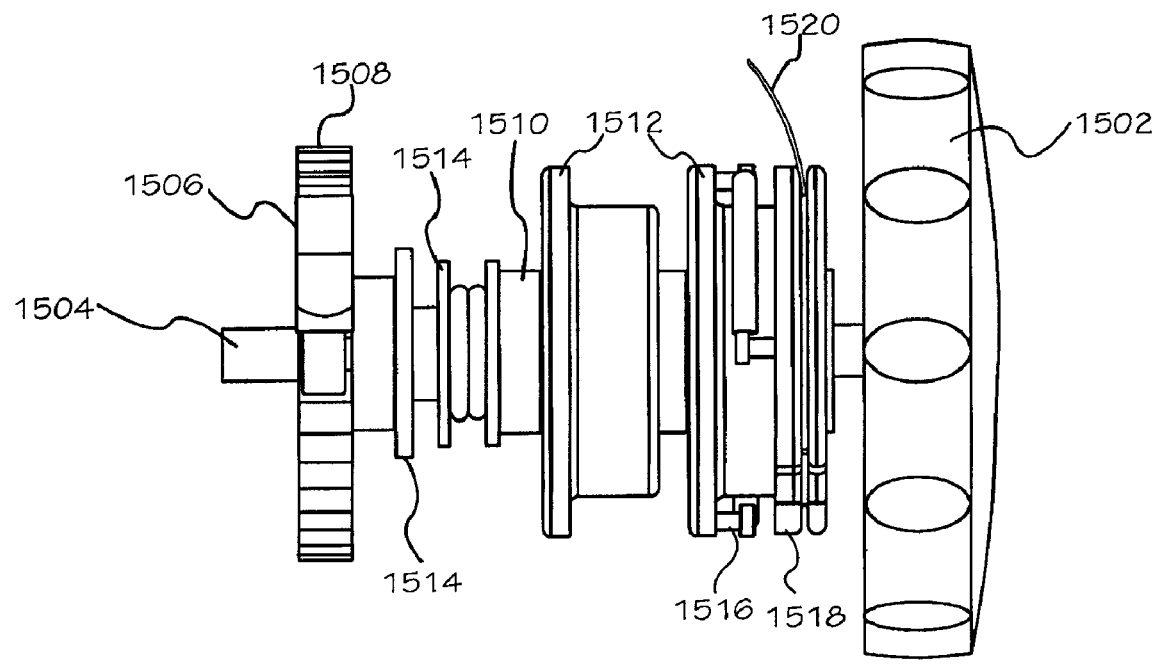
FIG. 16 is a side elevational view of the implant deployment tool of FIG. 15 with several elements removed.

FIGS. 15 and 16 show yet another embodiment of the invention used, e.g., to deliver and deploy a replacement heart valve or other medical implant. An actuator 1502 connects to a toothed ratchet wheel 1506 via a shaft 1504. A ratchet mechanism (not shown) extending from another portion of the deployment tool engages teeth 1508 of ratchet wheel 1506 to limit rotation of actuator 1502 to one direction. Also attached to shaft 1504 are three fixed clutch elements 1510. A spool clutch element 1512 surrounds each fixed clutch element 1510; the interface between the each fixed clutch element 1510 and spool clutch element 1512 pair forms sliding clutch friction surfaces 1514. A spool 1518 connects to each spool clutch element 1512 via a spring 1516. A medical implant deployment tool actuation element (such as a thread or control wire) is wound about and extends from each spool 1518. Actuator 1502 may be rotated in the direction permitted by the ratchet mechanism to, e.g., wind the actuation elements 1520 about the spools 1518. If the resistance force presented by an actuation element 1520 exceeds the slip point of the associated clutch (i.e., when the force on the actuation element exceeds the friction force provided by the clutch's friction surface), the clutch will slip and the spool 1518 will stop rotating. This friction point may be designed to slip at a force below the break point of the actuation element. In addition, use of a spring 1516 between the spool 1518 and its associated spool clutch element 1512 helps maintain tension on each actuation element. This embodiment provides for simultaneous actuation of multiple actuation elements with a single actuator.

Figure 17A:
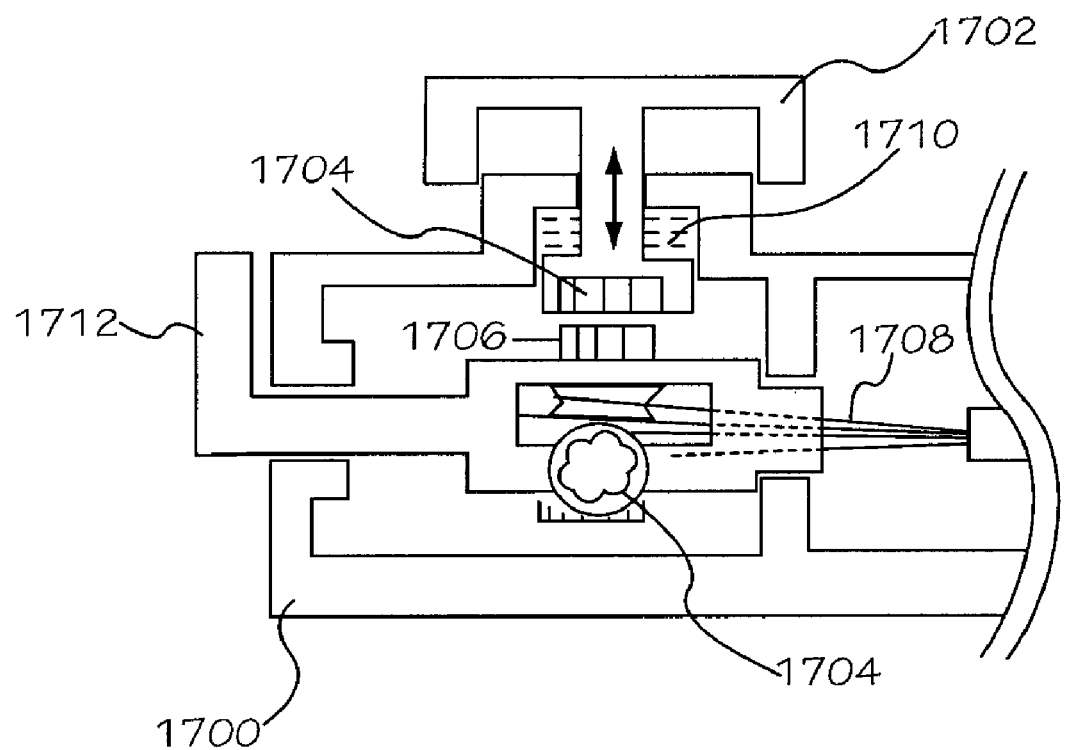
FIGS. 17A and 17B are schematic views of an implant deployment tool according to yet another embodiment of the invention showing a deployment tool actuator operating multiple actuation elements.
Figure 17B:
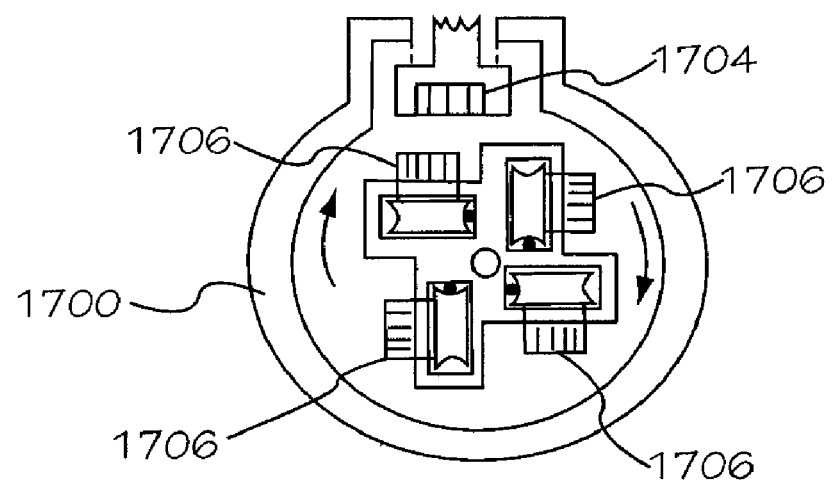

FIGS. 17A and 17B show still another embodiment of a medical implant deployment tool according to the invention. In this embodiment, the deployment tool's rotatable actuator 1702 has an actuator interface 1704 that can mate with a plurality of actuation element interfaces 1706, each connected to a different actuation element 1708. The actuator 1702 may be moved about the deployment tool handle 1700 to engage the different actuation element interfaces 1706 as desired. An indicator 1712 may be used to provide the user with information about the position of the actuator, e.g., the operation that will be performed when the actuator is in that position. The actuation element interfaces 1706 may be arranged in the handle 1700 in the order in which actuation steps are to be performed.

Figure 18A:
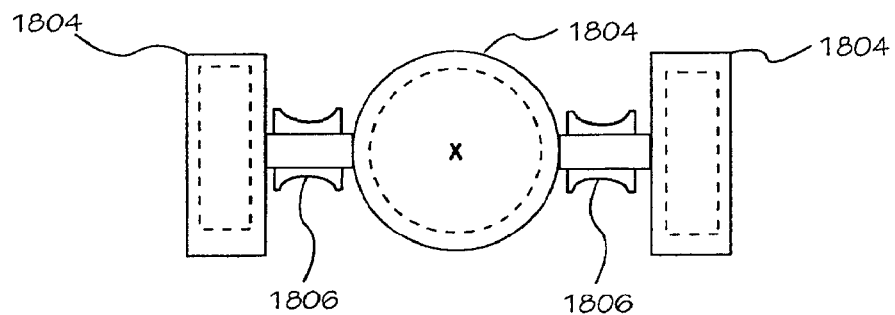
FIGS. 18A-18C are schematic views of an implant deployment tool according to still another embodiment of the invention showing a deployment tool actuator operating multiple actuation elements.
Figure 18B:
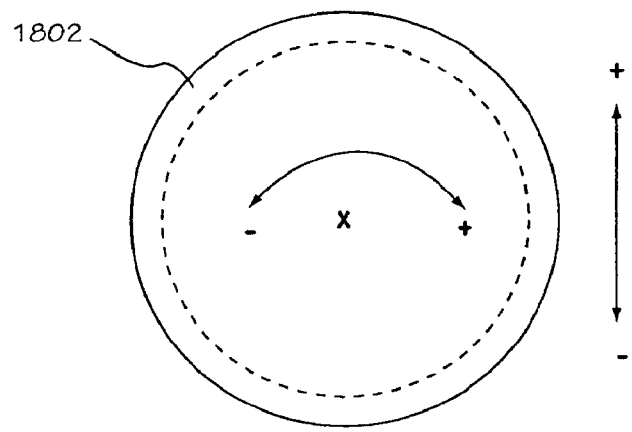
Figure 18C:
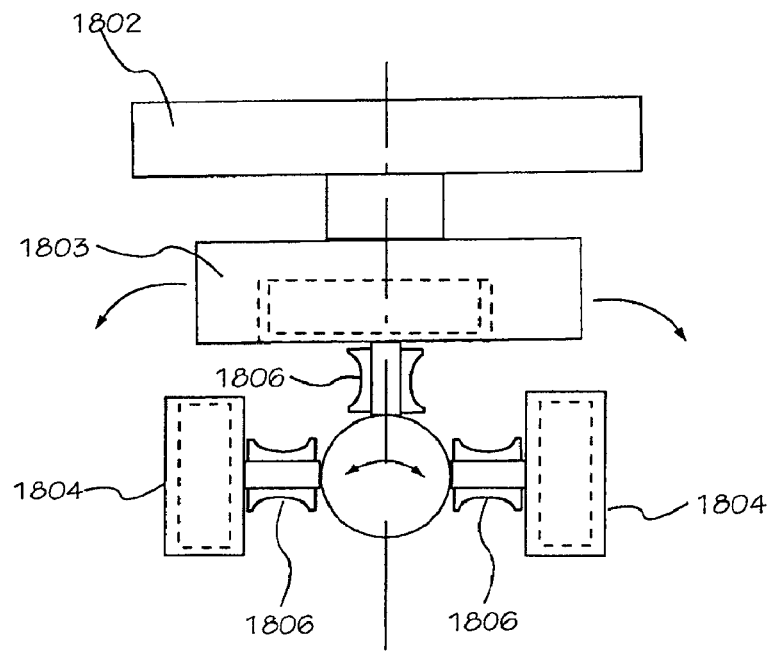

FIGS. 18A-18C show yet another embodiment of a medical implant deployment tool using a single actuator to operate a plurality of actuation elements. In this embodiment, actuator 1802 may be rotated to engage its actuator interface 1803 with one of a plurality of actuation element interfaces 1804. Each actuation element interfaces is connected to a spool 1806 about which an actuation element (not shown) may be wound. Once again, the actuation element interfaces 1804 may be arranged in the deployment tool handle in the order in which actuation steps are to be performed.

Figure 19A:
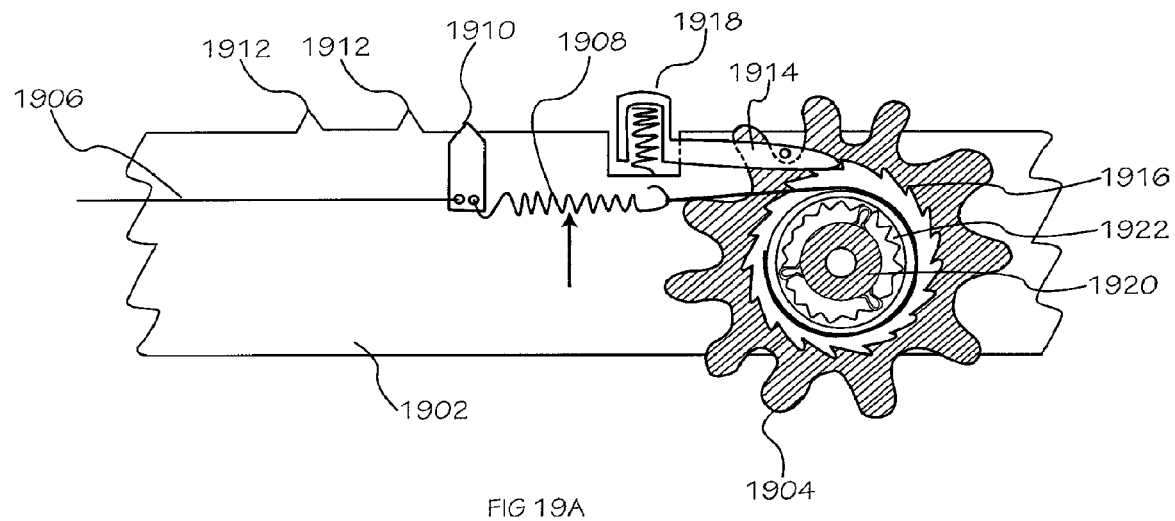
FIG. 19A is a schematic view of an implant deployment tool actuator and actuation element according to yet another embodiment of the invention.
Figure 19B:
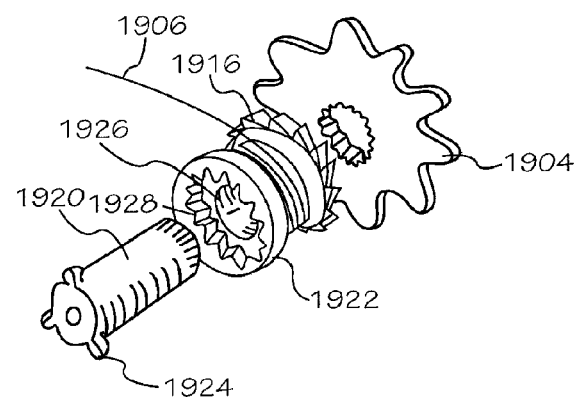
FIG. 19B is a partial exploded view of the implant deployment tool actuator and actuation element of FIG. 19A.

FIGS. 19A and 19B show another embodiment of the invention with a rotating actuator 1904 supported by a handle 1902. A ratchet element 1914 interacts with a toothed ratchet wheel 1916 to limit rotation of actuator 1902 to the clockwise direction, as shown in FIG. 19A. A spring biased ratchet release button 1918 may be depressed to release the ratchet and permit counterclockwise rotation of actuator 1904. A spool 1922 surrounds a center shaft 1920 which is connected to actuator 1904. Interior teeth 1928 of spool 1922 interact with deformable projections 1924 of shaft 1920 to form a clutch element; projections 1924 deform and slip between teeth 1928 when the rotation force between spool 1922 and shaft 1920 exceeds a designed slip level. An actuation element 1906 (used, e.g., to perform a medical implant deployment operation) winds about spool 1922 and has an optional spring portion 1908. Also extending from actuation element 1906 is an indicator 1910 which aligns with markings 1912 on the deployment tool handle to show the position of the actuation element.

Figure 20:
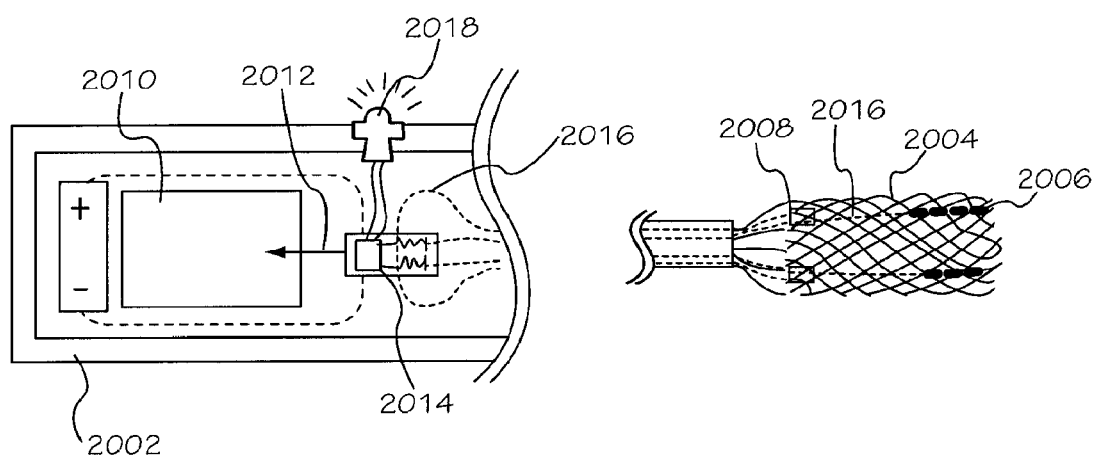
FIG. 20 shows part of an implant deployment tool with positive confirmation of actuation of an implant.

FIG. 20 shows an embodiment that provides feedback to the user of the completion of an implant deployment operation. In this example, the implant is a replacement heart valve (such as those described above) having an anchor 2004, posts 2006 and proximal locking elements 2008. An actuator 2010 (such as one of the actuators described above) within handle 2002 moves an actuation element 2012 which is connected (in a manner not shown in FIG. 20) to posts 2006. When actuator 2010 moves posts 2006 into locking elements 2008, an electrical connection is made through circuit controller 2041 and electrical conductors 2016 extending from the handle 2002 through the posts 2006 and locking elements 2008. Closing the electrical circuit powers an indicator light 2018 providing feedback to the user to show that posts 2006 have been inserted into locking elements 2008 and that the anchor is now locked.

Figure 21:
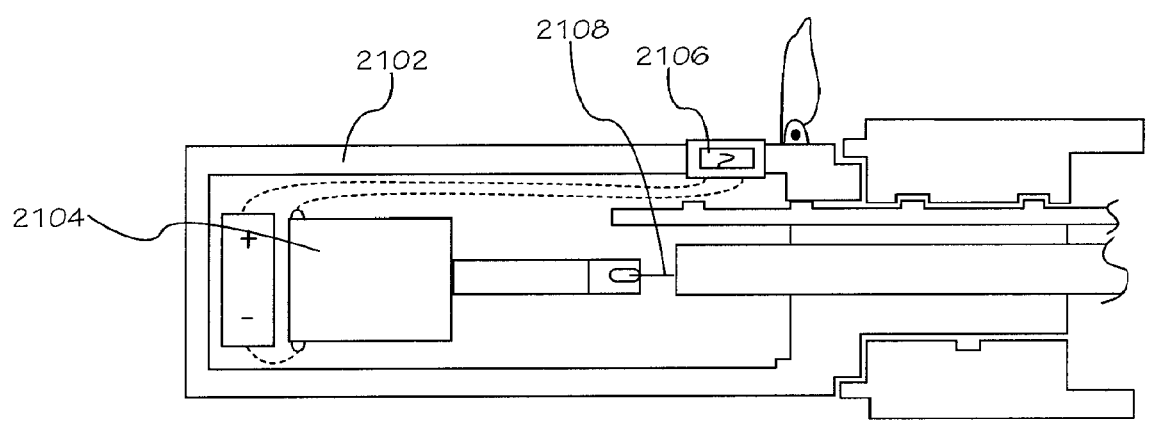
FIG. 21 shows part of a power operated implant deployment tool.

FIG. 21 shows an embodiment of the invention in which the deployment tool employs a power source within handle 2102, such as solenoid 2104, to move the actuation element 2108. Power source 2104 is actuated by depressing an actuator 2106. Actuation element 2108 may be moved to perform, e.g., a medical implant deployment operation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for endovascularly replacing a heart valve of a patient, the method comprising:
   endovascularly delivering a replacement heart valve implant comprising a replacement valve and an anchor within a sheath to an implant site; and
   deploying the replacement heart valve at the implant site with a deployment tool, wherein the deployment tool comprises an actuator which controls a first actuation element and a second actuation element,
   wherein during a first portion of the deployment step actuation of the actuator moves the first actuation element but does not move the second actuation element, and wherein during a second portion of the deployment step actuation of the actuator moves the first actuation element and the second actuation element,
   wherein the movement of the first actuation element during the first portion of the deployment step is initiated when the anchor is within the sheath, and wherein the movement of the second actuation element during the second portion of the deployment step is initiated after the anchor is outside of the sheath.

2. The method of claim 1 wherein movement of the actuator during the first portion of the deployment step moves the sheath with respect to the anchor.

3. The method of claim 1 further comprising using an actuator to release the anchor from the deployment tool.

4. The method of claim 1 wherein actuation of the actuator during the second portion of the deployment step locks the anchor in an expanded configuration.

5. The method of claim 1 further comprising actuating the actuator to unlock the anchor from a locked configuration.

6. The method of claim 1 further comprising actuating the actuator to move the replacement valve with respect to the anchor.

7. The method of claim 1 further comprising applying an outward pressure from expansion of the anchor to the implant site of at least about 7 psi.

8. The method of claim 1 whereon the actuator provides a mechanical advantage of at least about 2:1.

9. The method of claim 1 wherein the actuator provides a mechanical advantage that varies over an actuator movement range.

10. The method of claim 1 wherein an anchor actuation element operably connects the actuator with the anchor, the applying step comprising moving a distal end of the anchor actuation element at a variable speed as the actuator moves at a constant speed.

11. The method of claim 1 further comprising providing information about completion of actuation through a feedback mechanism.

12. The method of claim 1 wherein during the first portion of the deploying step, actuating of the actuator performs a first deployment step using the first actuation element and wherein during the second portion of the deploying step, actuation of the actuator performs a second deployment step using the second actuation element.

13. The method of claim 12 wherein the actuator is a first actuator, the performing step comprising performing the second replacement valve deployment operation with a second actuator.

14. The method of claim 13 further comprising performing a third replacement valve deployment operation with a third actuator, wherein the actuators are arranged in an operation order, the method further comprising the step of operating the actuators in the operation order.

15. The method of claim 12 wherein the actuator interfaces with the first and second actuation elements.

16. The method of claim 12 further comprising the step of operating an actuator interlock before operating the second actuation element.

17. The method of claim 1 wherein during the first portion of the deploying step actuation of the actuator moves the first actuation element axially.

18. The method of claim 17 wherein during the second portion of the deploying step actuation of the actuator moves the first and second actuation elements axially.

19. The method of claim 1 wherein actuation of the actuator during the first and second portion of the deployment step comprises rotating the actuator.

20. The method of claim 1 wherein actuation of the actuator to move the first actuation element performs a first deployment step and wherein actuation of the actuator to move the second actuation element performs a second deployment step.

21. A method for endovascularly replacing a heart valve of a patient, the method comprising:
  endovascularly delivering a replacement heart valve to an implant site within the patient, wherein the replacement heart valve comprises an expandable anchor and a replacement valve; and
  deploying the replacement heart valve at the implant site with a delivery tool, wherein the delivery tool comprises an actuator disposed external to the patient which controls a first actuation element and a second actuation element,
  wherein during a first portion of the deploying step actuation of the actuator external to the patient moves the first actuation element independently of the second actuation element, and wherein during a second portion of the deployment step actuation of the actuator external to the patient moves the first actuation element and the second actuation element dependently,
  wherein during the first portion of the deploying step actuation of the actuator comprises moving the actuator in a first direction, and wherein during the second portion of the deployment step actuation of the actuator to move the first actuation element and the second actuation element dependently comprises moving the actuator in the first direction.

22. The method of claim 21 wherein during the first portion of the deploying step actuation of the actuator moves the first actuation element axially.

23. The method of claim 22 wherein during the second portion of the deploying step actuation of the actuator moves the first and second actuation elements axially.

24. The method of claim 21 wherein actuation of the actuator in the first direction comprises rotating the actuator.

25. The method of claim 21 wherein actuation of the actuator to move the first actuation element performs a first deployment step and wherein actuation of the actuator to move the second actuation element performs a second deployment step.

26. The method of claim 1 wherein the actuator is disposed on a handle external to the patient, and wherein the deployment step comprises actuation of the actuator external to the patient.

27. The method of claim 26 wherein actuation of the actuator in the first and second portions of the deployment step comprises actuation of the actuator in a singular type of motion.

28. The method of claim 21 wherein moving the actuator during the first portion of the deployment step moves the sheath with respect to the anchor.

29. A method for endovascularly replacing a heart valve of a patient, the method comprising:
  endovascularly delivering a replacement heart valve to an implant site within the patient, wherein the replacement heart valve comprises an expandable anchor and a replacement valve;
  deploying the replacement heart valve at the implant site with a delivery tool, wherein the delivery tool comprises an actuator disposed external to the patient that controls a first actuation element and a second actuation element;
  actuating the actuator external to the patient during a first portion of the deploying step to move the first actuation element independently of the second actuation element; and
  actuating the actuator external to the patient during a second portion of the deploying step to move the first actuation element and the second actuation element dependently,
  wherein actuating the actuator during the first and second portions of the deploying step comprises actuating the actuator in a singular type of motion.

30. The method of claim 29 wherein the first portion of the deploying step occurs before the second portion of the deploying step.

31. The method of claim 29 wherein actuating the actuator during the first portion of the deploying step to move the first actuation element comprises moving the first actuation element axially.

32. The method of claim 29 wherein actuating the actuator external to the patient during the second portion of the deploying step comprises moving the first actuation element and the second actuation element axially.

33. The method of claim 29 wherein actuating the actuator external to the patient during the first portion of the deploying step releases the expandable anchor from within a delivery sheath.

34. The method of claim 29 wherein actuating the actuator external to the patient during the first portion of the deploying step comprises moving a delivery sheath proximally relative to the expandable anchor.

35. The method of claim 29 wherein actuating the actuator during the second portion of the deploying step to move the first actuation element and the second actuation element dependently occurs after the expandable anchor is released from a delivery sheath.

36. The method of claim 29 wherein actuating the actuator external to the patient during the second portion of the deploying step to move the first actuation element and the second actuation element dependently comprises foreshortening the expandable anchor.

37. The method of claim 29 wherein actuating the actuator external to the patient during the second portion of the deploying step to move the first actuation element and the second actuation element dependently comprises moving a first anchor locking element towards a second anchor locking element.

38. The method of claim 29 wherein the singular type of motion comprises rotation in a first direction.

39. The method of claim 29 wherein actuating the actuator external to the patient during a first portion of the deploying step to move the first actuation element independently of the second actuation element comprises moving a delivery sheath proximal relative to the expandable anchor, and wherein actuating the actuator external to the patient during the second portion of the deploying step to move the first actuation element and the second actuation element dependently comprises moving the delivery sheath proximal relative to the expandable anchor and foreshortening the expandable anchor.

* * * * *